United States Patent
Staby

(12)
(10) Patent No.: US 6,444,788 B1
(45) Date of Patent: Sep. 3, 2002

(54) ION EXCHANGE CHROMATOGRAPHY OF GLP-1, ANALOGS AND DERIVATIVES THEREOF

(75) Inventor: Arne Staby, Bagsværd (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 09/523,785

(22) Filed: Mar. 13, 2000

Related U.S. Application Data

(60) Provisional application No. 60/125,888, filed on Mar. 24, 1999, and provisional application No. 60/179,356, filed on Jan. 31, 2000.

(30) Foreign Application Priority Data

| Mar. 15, 1999 | (DK) | 1999 00361 |
|---|---|---|
| Jan. 19, 2000 | (DK) | 2000 00082 |

(51) Int. Cl.[7] .................. A61K 38/00; A23J 1/00; C07K 1/00

(52) U.S. Cl. .................. 530/344; 530/416; 530/417; 530/324; 514/12

(58) Field of Search .................. 530/308, 303, 530/416, 417, 324, 344; 514/12, 866

(56) References Cited

U.S. PATENT DOCUMENTS

| 3,907,676 A | 9/1975 | Jorgensen | 210/31 C |
| 4,129,560 A | 12/1978 | Zoltobrocki | 260/112 |
| 4,361,510 A | 11/1982 | Mitra | 260/112 |
| 5,101,013 A | 3/1992 | Dorschug et al. | 530/305 |

FOREIGN PATENT DOCUMENTS

| EP | 0 207 727 A2 | 1/1987 |
| EP | 0 699 686 A2 | 3/1996 |
| EP | 0 708 179 A2 | 4/1996 |
| WO | WO 87/06941 | 11/1987 |
| WO | WO 90/11296 | 10/1990 |
| WO | WO 91/11457 | 8/1991 |
| WO | WO 96/32414 | 10/1996 |
| WO | WO 98/08871 | 3/1998 |
| WO | WO 98/08872 | 3/1998 |

OTHER PUBLICATIONS

Bataille et al., "Isolation of glucagon–37 (bioactive enteroglucagon/oxyntomodium) from porcine jejuno–ileum", Sep. 1982, FEBS Letters, vol. 146, No. 1, pp 73–78.*

M. Raida et al., "Liquid Chromatography and Electrospray Mass Spectrometric Mappings of Peptides from Human Plasma Filtrate" Journ Of American Society of Mass Spectrometry, vol. 10, pp. 45–54 (1999).

Huskins et al., "Halibut Muscle 3–Phosphoglycerate Kinase. Chemical And Physical Properties of the Enzyme and Its Substrate Complexes" Biochemistry, vol. 21., pp. 4180–4189 (1982).

Brange et al., Acta Pharm. Nord., vol. 4, No. 4, pp. 223–232 (1992).

Schmidt et al., Diabetologia, vol. 28, pp. 704–707 (1985).

Kagaku et al., Research Disclosure, pp. 564–565 (Sep. 1986).

Abstract of Japanese Patent JP 10059866.

Abstract of Japanese Patent JP 10059867.

Abstract of Dizdaroglu et al., Journal of Chromatography, vol. 237, pp. 417–428 (1982).

Abstract of Stadalius et al., Journal of Chromatography, vol. 387, pp. 21–40 (1987).

* cited by examiner

*Primary Examiner*—Karen Cochrane Carlson
*Assistant Examiner*—Rita Mitra
(74) *Attorney, Agent, or Firm*—Reza Green, Esq.; Richard Bork, Esq.

(57) ABSTRACT

The present invention relates to an ion exchange chromatography process for purifying GLP-1 or an analog or a derivative thereof from a mixture containing said GLP-1 and related impurities, and to an industrial method including such ion exchange chromatography process.

9 Claims, 14 Drawing Sheets

Figure 1:
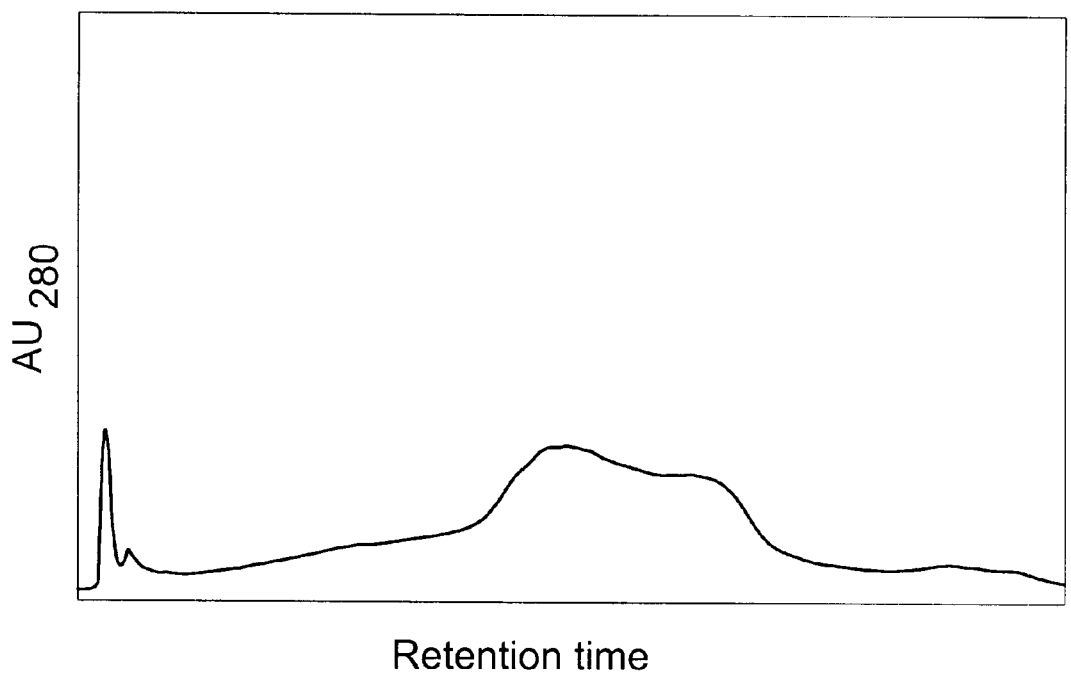

Chromatogram of Example 22.

Chromatogram of Example 1.

Chromatogram of Example 4.

Chromatogram of Example 5.

Analytical chromatogram of Example 5. Sample for application.

Chromatogram of Example 6.

Chromatogram of Example 10.

Chromatogram of Example 11.

Chromatogram of Example 13.

Chromatogram of Example 17.

Chromatogram of Example 18.

Chromatogram of Example 19.

Chromatogram of Example 21.

Chromatogram of Example 22.

ION EXCHANGE CHROMATOGRAPHY OF GLP-1, ANALOGS AND DERIVATIVES THEREOF

CROSS-REFERENCE TO RELATED APPLICATIONS

This application claims priority under 35 U.S.C. 119 of Danish applications PA 1999 00361 filed Mar. 15, 1999 and PA 2000 00082 filed Jan. 19, 2000, and of U.S. Provisional applications 60/125,888 filed Mar. 24, 1999 and 60/179,356 filed Jan. 31, 2000, the contents of which are fully incorporated herein by reference.

FIELD OF THE INVENTION

The present invention relates to an ion exchange chromatography process for purifying GLP-1 or an analog or a derivative thereof from a mixture containing said GLP-1 and related impurities, and to an industrial method including such ion exchange chromatography process.

BACKGROUND

For the purification and analysis of proteins and peptides, chromatography is a well-known and widely used method. A number of different chromatographic principles are applied, among these ion exchange chromatography (IEC). The IEC principle includes two different approaches: anion exchange and cation exchange according to the charge of the ligands on the ion exchange resin. A conventional IEC purification process usually consists of one or more: equilibration sections, application or loading sections, wash sections, elution sections, and regeneration sections (cf. Remington's Pharmaceutical Sciences, Gennaro, ed., Mack Publishing Co., Easton, Pa., 1990, or Remington: The Science and Practice of Pharmacy, 19th Edition (1995)).

The main principle of elution in IEC in industrial purification processes is salt component gradients in an aqueous buffer solution at constant pH, either as step or linear gradients (cf. S. Bjørn and L. Thim, Activation of Coagulation Factor VII to VIIa, Res. Discl. No. 269, 564–565, 1986). Isocratic elution is possible, but seldom used. Organic solvents or modifiers have occasionally been added to the solutions to keep the protein or peptide on the desired form or just in solution (cf. K. H. Jørgensen, Process for Purifying Insulin, U.S. Pat. No. 3,907,676, Sep. 23, 1975; and J. Brange, O. Hallund and E. Sørensen, Chemical Stability of Insulin 5. Isolation, Characterisation and Identification of Insulin Transformation Products, Acta Pharm. Nord. 4(4), 223–232, 1992).

Glucagon-Like Peptide-1 (GLP-1) (cf. Schmidt et al. in Diabetologia 28 704–707, 1985) and analogues as well as derivatives thereof may be used in the treatment of diabetes, as disclosed in WO 98/08871. A GLP-1 peptide and related analogues are easily dissolved in aqueous solvents and kept in a monomized form. Traditional IEC purification of GLP-1 with salt gradients in aqueous solvents may, however, be problematic due to the lack of selectivity between a GLP-1 target moiety and related impurities.

WO 87/06941 (The General Hospital Corporation) disclose peptide fragments which comprises GLP-1(7-37) and functional derivatives thereof and to its use as an insulinotropic agent.

WO 90/11296 (The General Hospital Corporation) disclose peptide fragments which comprise GLP-1(7-36) and functional derivatives thereof and have an insulinotropic activity which exceeds the insulinotropic activity of GLP-1(1-36) or GLP-1 (1-37) and to their use as insulinotropic agents.

WO 91/11457 (Buckley et al.) discloses analogues of the active GLP-1 peptides 7-34, 7-35, 7-36, and 7-37.

WO 98/08871 discloses GLP-1 derivatives in which a lipophilic substituent is attached to at least one amino acid residue. The lipophilic substituents are in particular long-chain groups containing e.g. 12 24 carbon atoms.

WO 98/08872 discloses GLP-2 derivatives in which a lipophilic substituent is attached to at least one amino acid residue. The lipophilic substituents are in particular long-chain groups containing e.g. 12–24 carbon atoms.

WO 96/32414 discloses GLP-2 analogues.

EP 0699686-A2 (Eli Lilly & Co.) discloses certain N-terminal truncated fragments of GLP-1 that are reported to be biologically active.

EP 0708179-A2 (Eli Lilly & Co.) discloses GLP-1 analogues and derivatives that include an N-terminal imidazole group and optionally an unbranched $C_6$–$C_{10}$ acyl group in attached to the lysine residue in position 34.

DESCRIPTION OF THE INVENTION

In contrast to the above described IEC techniques for purification of any protein or peptide, consisting of one or more equilibration steps, application or loading steps, wash steps, elution steps, and regeneration steps, the instant invention relates to the use of an organic modifier for the purification of a GLP-1 peptide and all related analogues etc. by IEC. By addition of an organic modifier especially to the elution section of the IEC purification step, an increase in selectivity and efficiency is obtained compared to the same run with aqueous buffers, both for anion and cation exchange chromatography. The equilibration solution and the sample for application may or may not contain the organic modifier. The use of an organic modifier has the additional advantage that no salt or very low concentrations of salt is needed for elution, especially for cation exchange chromatography compared to an aqueous chromatographic system.

In a broad aspect the present invention relates to a cation exchange chromatography process for purifying a peptide from a mixture comprising said peptide and related impurities, comprising the step of:

separating said peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities.

In another broad aspect the present invention relates to a cation exchange chromatography process for purifying a peptide from a mixture comprising said peptide and related impurities, comprising the step of:

separating said peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities.

In another broad aspect the present invention relates to an anion exchange chromatography process for purifying a peptide from a mixture comprising said peptide and related impurities, comprising the step of:

separating said peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities.

In another broad aspect the present invention relates to an anion exchange chromatography process for purifying a peptide from a mixture comprising said peptide and related impurities, comprising the step of:

separating said peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities.

In an embodiment of the present invention the peptide to be purified is selected from polypeptides, oligopeptides, proteins, receptors, vira, as well as homologues, analogues and derivatives thereof, preferably glucagon, hGH, insulin, aprotinin, FactorVII, TPA, FactorVIIa (NovoSeven®, available from Novo Nordisk A/S, Bagsvaerd, Denmark), FactorVIIa, FFR-FactorVIIa, heparinase, ACTH, Heparin Binding Protein, corticotropin-releasing factor, angiotensin, calcitonin, insulin, glucagon-like peptide-1 (GLP-1), glucagon-like peptide-2 (GLP-2), insulin-like growth factor-1, insulin-like growth factor-2, fibroblast growth factors, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, DPP IV, interleukins, immunoglobulins, complement inhibitors, serpin protease inhibitors, cytokines, cytokine receptors, PDGF, tumor necrosis factors, tumor necrosis factors receptors, growth factors and analogues as well as derivatives thereof, more preferably glucagon, hGH, insulin, aprotinin, FactorVII, FactorVIIa, FFR-FactorVIIa, heparinase, glucagon-like peptide-1, glucagon-like peptide-2 and analogues as well as derivatives thereof, such as $Arg^{34}GLP$-1(7-37), human insulin, and B28lsoAsp insulin. Each of these peptides constitutes an alternative embodiment of the present invention.

Accordingly, an aspect of the present invention relates to a cation exchange chromatography process for purifying a GLP-1 peptide from a mixture comprising said peptide and related impurities, comprising the step of:

separating said GLP-1 peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities.

Another aspect of the present invention relates to a cation exchange chromatography process for purifying a GLP-1 peptide from a mixture comprising said peptide and related impurities, comprising the step of:

separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities.

Another aspect of the present invention relates to an anion exchange chromatography process for purifying a GLP-1 peptide from a mixture comprising said peptide and related impurities, comprising the step of:

separating said GLP-1 peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities.

Another aspect of the present invention relates to an anion exchange chromatography process for purifying a GLP-1 peptide from a mixture comprising said peptide and related impurities, comprising the step of:

separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities.

The elution in above aspects may also be possible by changing the content of organic modifier in the elution section, which is considered an embodiment of the present invention.

The linear or step gradient in the salt component would be from a lower to a higher concentration in both IEC modes.

In the above aspects of the present process the elution could also be considered a washing step of related impurities.

In one embodiment of the present invention the ratio of organic modifier to water, on a weight percent basis, is from 1:99 to 99:1, such as 1:99 to 80:20, 20:80 to 80:20, 30:70 to 70:30, 35:50 to 50:35, or 40:50 to 50:40. Each of these ratios constitutes an alternative embodiment of the present invention.

In another embodiment of the present invention the organic modifier is selected from $C_{1-6}$-alkanol, $C_{1-6}$-alkenol or $C_{1-6}$-alkynol, urea, guanidine, or $C_{1-6}$-alkanoic acid, such as acetic acid, $C_{2-6}$-glycol, $C_{3-7}$-polyalcohol including sugars, preferably $C_{1-6}$-alkanol and $C_{2-6}$-glycol, more preferably methanol, ethanol, propanols and butanols and hexyl glycols, most preferably ethanol and 2-propanol. Each of these organic modifiers constitutes an alternative embodiment of the present invention.

In a further embodiment of the present invention the step or linear pH gradient for the anion exchange chromatography process goes from a higher to a lower pH.

In a further embodiment of the present invention the step or linear pH gradient for the cation exchange chromatography process goes from a lower to a higher pH.

In a further embodiment of the present invention the salt component is selected from any organic or inorganic salt and mixtures thereof, preferably NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof, most preferred sodium acetate, potassium acetate, ammonium acetate, NaCl, $NH_4Cl$, KCl. Each of these salt components constitutes an alternative embodiment of the present invention.

In a further embodiment of the present invention the gradient in salt component is a step gradient in salt component.

In a further embodiment of the present invention the salt component is present in a step concentration selected from the range of 0.1 mmol/kg to 3000 mmol/kg, preferably 1 mmol/kg to 1000 mmol/kg, more preferably 5 mmol/kg to 500, most preferably 20 mmol/kg to 300 mmol/kg. Each of these ranges constitutes an alternative embodiment of the present invention.

In a further embodiment of the present invention the gradient in salt component is a linear gradient in salt component.

In a further embodiment of the present invention the salt component is present in a linear concentration selected from 0.1 mmol/kg to 3000 mmol/kg, preferably 1 mmol/kg to 1000 mmol/kg, more preferably 5 mmol/kg to 500, most preferably 20 mmol/kg to 300 mmol/kg. Each of these linear concentrations constitutes an alternative embodiment of the present invention.

In a further embodiment of the present invention no salt component is present.

In a further embodiment of the present invention the buffer is selected from citrate buffers, phosphate buffers, tris buffers, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, triethanol amine, imidazole buffers, pyridine buffers and barbiturate buffers and mixtures thereof, preferably citric acid, sodium citrate, potassium citrate, sodium phosphate, potassium phosphate, phosphorous acid, glutamic acid, sodium glutamate, potassium glutamate, glycin, sodium carbonate, tris-hydroxymethyl amino methane and boric acid and mixtures thereof. Each of these buffers constitutes an alternative embodiment of the present invention.

In a further embodiment of the present invention the buffer is present in a concentration selected from the range of 0.1 mmol/kg to 500 mmol/kg, preferably 1 mmol/kg to 200 mmol/kg, more preferably 5 mmol/kg to 100 mmol/kg, most preferably 10 mmol/kg to 50 mmol/kg. Each of these ranges constitutes an alternative embodiment of the present invention.

In a further embodiment of the present invention no buffer is present.

In a further embodiment of the present invention the GLP-1 peptide to be purified is selected from GLP-1 (7-37), GLP-1 (7-36) amide as well as analogues and derivatives thereof, in particular but not limited to human glucagon-like peptide-1, $Arg^{26}$-GLP-1 (7-37); $Arg^{34}$-GLP-1(7-37); $Lys^{36}$-GLP-1(7-37); $Arg^{26,36}Lys^{36}$-GLP-1(7-37); $Arg^{26,34}Lys^{38}$-GLP-1(7-38); $Arg^{26,34}Lys^{39}$-GLP-1(7-39); $Arg^{26,34}Lys^{40}$-GLP-1(7-40); $Arg^{26}Lys^{36}$-GLP-1(7-37); $Arg^{34}Lys^{36}$-GLP-1(7-37); $Arg^{26}Lys^{39}$-GLP-1(7-39); $Arg^{34}Lys^{40}$-GLP-1(7-40); $Arg^{26,34}Lys^{36,39}$-GLP-1(7-39); $Arg^{26,34}Lys^{36,40}$-GLP-1(7-40); $Gly^8Arg^{26}$-GLP-1 (7-37); $Gly^8Arg^{34}$GLP-1 (7-37); $Gly^8Lsy^{36}$-GLP1(7-37); $Gly^8Arg^{26,34}Lys^{36}$-GLP-1(7-37); $Gly^8Arg^{26,34}Lys^{39}$-GLP-1(7-39); $Gly^8Arg^{26,34}Lys^{40}$-GLP-1(7-40); $Gly^8Arg^{26}Lys^{36}$-GLP-1(7-37); $Gly^8Arg^{34}Lys^{36}$-GLP-1(7-37); $Gly^8Arg^{26}Lys^{39}$-GLP-1(7-39); $Gly^8Arg^{34}Lys^{40}$-GLP-1(7-40); $Gly^8Arg^{26,34}Lys^{36,39}$-GLP-1(7-39); $Gly^8Arg^{26,34}Lys^{36,40}$-GLP-1(7-40); $Arg^{26,34}Lys^{38}$GLP-1(7-38); $Arg^{26,34}Lys^{39}$GLP-1(7-39); $Arg^{26,34}Lys^{40}$GLP-1(7-40); $Arg^{26,34}Lys^{41}$GLP-1(7-41); $Arg^{26,34}Lys^{42}$GLP-1(7-42); $Arg^{26,34}Lys^{43}$GLP-1(7-43); $Arg^{26,34}Lys^{44}$GLP-1(7-44); $Arg^{26,34}Lys^{45}$GLP-1(7-45); $Arg^{26,34}Lys^{38}$GLP-1(1-38); $Arg^{26,34}Lys^{39}$GLP-1(1-39); $Arg^{26,34}Lys^{40}$GLP-1(1-40); $Arg^{26,34}Lys^{41}$GLP-1(1-41); $Arg^{26,34}Lys^{42}$GLP-1(1-42); $Arg^{26,34}Lys^{43}$GLP-1(1-43); $Arg^{26,34}Lys^{44}$GLP-1(1-44); $Arg^{26,34}Lys^{45}$GLP-1(1-45); $Arg^{26,34}Lys^{38}$GLP-1(2-38); $Arg^{26,34}Lys^{39}$GLP-1(2-39); $Arg^{26,34}Lys^{40}$GLP-1(2-40); $Arg^{26,34}Lys^{41}$GLP-1(2-41); $Arg^{26,34}Lys^{42}$GLP-1(2-42); $Arg^{26,34}Lys^{43}$GLP-1(2-43); $Arg^{26,34}Lys^{44}$GLP-1(2-44); $Arg^{26,34}Lys^{45}$GLP-1(2-45); $Arg^{26,34}Lys^{38}$GLP-1(3-38); $Arg^{26,34}Lys^{39}$GLP-1(3-39); $Arg^{26,34}Lys^{40}$GLP-1(3-40); $Arg^{26,34}Lys^{41}$GLP-1(3-41); $Arg^{26,34}Lys^{42}$GLP-1(3-42); $Arg^{26,34}Lys^{43}$GLP-1(3-43); $Arg^{26,34}Lys^{44}$GLP-1(3-44); $Arg^{26,34}Lys^{45}$GLP-1(3-45); $Arg^{26,34}Lys^{38}$GLP-1(4-38); $Arg^{26,34}Lys^{39}$GLP-1(4-39); $Arg^{26,34}Lys^{40}$GLP-1(4-40); $Arg^{26,34}Lys^{41}$GLP-1(4-41); $Arg^{26,34}Lys^{42}$GLP-1(4-42); $Arg^{26,34}Lys^{43}$GLP-1(4-43); $Arg^{26,34}Lys^{44}$GLP-1(4-44); $Arg^{26,34}Lys^{45}$GLP-1(4-45); $Arg^{26,34}Lys^{38}$GLP-1(5-38); $Arg^{26,34}Lys^{39}$GLP-1(5-39); $Arg^{26,34}Lys^{40}$GLP-1(5-40); $Arg^{26,34}Lys^{41}$GLP-1(5-41); $Arg^{26,34}Lys^{42}$GLP-1(5-42); $Arg^{26,34}Lys^{43}$GLP-1(5-43); $Arg^{26,34}Lys^{44}$GLP-1(5-44); $Arg^{26,34}Lys^{45}$GLP-1(5-45); $Arg^{26,34}Lys^{38}$GLP-1(6-38); $Arg^{26,34}Lys^{39}$GLP-1(6-39); $Arg^{26,34}Lys^{40}$GLP-1(6-40); $Arg^{26,34}Lys^{41}$GLP-1(6-41); $Arg^{26,34}Lys^{42}$GLP-1(6-42); $Arg^{26,34}Lys^{43}$GLP-1(6-43); $Arg^{26,34}Lys^{44}$GLP-1(6-44); $Arg^{26,34}Lys^{45}$GLP-1(6-45); $Arg^{26}Lys^{38}$GLP-1(1-38); $Arg^{34}Lys^{38}$GLP-1(1-38); $Arg^{26,34}Lys^{36,38}$GLP-1(1-38); $Arg^{32}Lys^{38}$GLP-1(7-38) $Arg^{34}Lys^{38}$GLP-1(1-38); $Arg^{34}Lys^{38}$GLP-1(1-38); $Arg^{26,34}Lys^{36,38}$GLP-1(7-38); $Arg^{26,34}Lys^{38}$GLP-1(7-38); $Arg^{26}Lys^{39}$GLP-1(1-39); $Arg^{343}Lys^{39}$GLP-1(1-39); $Arg^{26,34}$ $Lys^{36,39}$GLP-1(1-39); $Arg^{26}Lys^{39}$GLP-1(7-39); $Arg^{34}Lys^{39}$GLP-1(7-39); $Arg^{26,34}Lys^{36,39}$GLP-1(7-39); $Arg^{26}$-GLP-1(8-37); $Arg^{34}$-GLP-1(8-37); $Lys^{36}$-GLP-1(8-37); $Arg^{26,34}Lys^{36}$-GLP-1(8-37); $Arg^{26,34}Lys^{38}$GLP-1(8-38); $Arg^{26,34}Lys^{39}$-GLP-1(8-39); $Arg^{26,34}Lys^{40}$-GLP-1(8-40); $Arg^{26}Lys^{36}$-GLP1(8-37); $Arg^{34}Lys^{36}$-GLP-1(8-37); $Arg^{26}Lys^{39}$-GLP-1(8-39); $Arg^{34}Lys^{40}$-GLP-1(8-40); $Arg^{26,34}Lys^{36,39}$-GLP-1(8-39); $Arg^{26,34}Lys^{36,40}$-GLP-1(8-40); $Gly^8Arg^{26}$-GLP-1(8-37); $Gly^8Arg^{34}$-GLP-1(8-37); $Gly^8Lys^{36}$-GLP-1(8-37); $Gly^8Arg^{26,34}Lys^{36}$-GLP-1(8-37); $Gly^8Arg^{26,34}Lys^{39}$-GLP-1(8-39); $Gly^8Arg^{26,34}Lys^{40}$-GLP-1(8-40); $Gly^8Arg^{26}Lys^{36}$-GLP-1(8-37); $Gly^8Arg^{34}Lys^{36}$-GLP-1(8-37); $Gly^8Arg^{26}Lys^{39}$-GLP-1(8-39); $Gly^8Arg^{34}Lys^{40}$-GLP-1(8-40); $Gly^8Arg^{26,34}Lys^{36,39}$-GLP-1(8-39); $Gly^8Arg^{26,34}Lys^{36,40}$-GLP-1(8-40); $Arg^{26,34}$ Lys$^{38}$GLP-1(8-38); Arg$^{26,34}$Lys$^{39}$GLP-1(8-39); Arg$^{26,34}$Lys$^{40}$GLP-1(8-40); Arg$^{26,34}$Lys$^{41}$GLP-1(8-41); Arg$^{26,34}$Lys$^{42}$GLP-1(8-42); Arg$^{26,34}$Lys$^{43}$GLP-1(8-43); Arg$^{26,34}$Lys$^{44}$GLP-1(8-44); Arg$^{26,34}$Lys$^{45}$GLP-1(8-45); Arg$^{26}$Lys$^{38}$GLP-1(8-38); Arg$^{34}$Lys$^{38}$GLP-1(8-38); Arg$^{26,34}$Lys$^{36,38}$GLP-1(8-38); Arg$^{26,34}$Lys$^{38}$GLP-1(8-38); Arg$^{26}$Lys$^{39}$GLP-1(8-39); Arg$^{34}$Lys$^{39}$GLP-1(8-39); Arg$^{26,34}$Lys$^{36,39}$GLP-1(8-39); Arg$^{26}$-GLP-1(8-37), Arg$^{34}$-GLP-1(8-37), Lys$^{36}$-GLP-1(8-37), Arg$^{26,34}$Lys$^{36}$-GLP-1(8-37), Arg$^{26}$Lys$^{36}$-GLP-1(8-37), Arg$^{34}$Lys$^{36}$-GLP-1(8-37), Gly$^{8}$Arg$^{26}$-GLP-1(8-37), Gly$^{8}$Arg$^{34}$-GLP-1(8-37), Gly$^{8}$Lys$^{36}$-GLP-1(8-37), Gly$^{8}$Arg$^{26,34}$Lys$^{36}$-GLP-1(8-37), Gly$^{8}$Arg$^{26}$Lys$^{36}$GLP-1(8-37), Gly$^{8}$Arg$^{34}$Lys$^{36}$GLP-1(8-37); Arg$^{26}$Lys$^{38}$-GLP-1(8-38), Arg$^{26,34}$Lys$^{38}$-GLP-1(8-38), Arg$^{26,34}$Lys$^{36,38}$-GLP-1(8-38), Gly$^{8}$Arg$^{26}$Lys$^{38}$-GLP-1(8-38); Gly$^{8}$Arg$^{26,34}$Lys$^{36,38}$-GLP-1(8-38); Arg$^{34}$Lys$^{40}$-GLP-1(8-40), Arg$^{26,34}$Lys$^{26,40}$-GLP-1(8-40), Gly$^{8}$Arg$^{34}$Lys$^{40}$-GLP-1(8-40); Gly$^{8}$Arg$^{26,34}$Lys$^{36,40}$-GLP-1(8-40); Arg$^{26}$-GLP-1(8-36); Arg$^{34}$-GLP-1(8-36); Arg$^{26,34}$Lys$^{36}$-GLP-1(8-36); Arg$^{26}$-GLP-1(8-36)amide; Arg$^{34}$-GLP-1(8-36)amide; Arg$^{26,34}$Lys$^{36}$-GLP-1(8-36)amide; Arg$^{26}$-GLP-1(8-37); Arg$^{34}$-GLP-1(8-37); Arg$^{26,34}$Lys$^{36}$-GLP-1(8-37); Arg$^{26}$-GLP-1(8-38); Arg34-GLP-1(8-38); Arg$^{26,34}$Lys$^{38}$GLP-1(8-38); Arg$^{26}$-GLP-1(8-39); Arg$^{34}$-GLP-1(8-39); Arg$^{26,34}$Lys$^{39}$-GLP-1(8-39); Gly$^{8}$Arg$^{26}$-GLP-1(8-36); Gly$^{8}$Arg$^{34}$-GLP-1(8-36); Gly$^{8}$Arg$^{26,34}$Lys-GLP-1(8-36); Gly$^{8}$Arg$^{26}$-GLP-1(8-36)amide; Gly$^{8}$Arg$^{34}$-GLP-1(8-36)amide; Gly$^{8}$Arg$^{26,34}$Lys$^{36}$-GLP-1(8-36)amide; Gly$^{8}$Arg$^{26}$-GLP-1(8-37); Gly$^{8}$Arg$^{34}$-GLP-1(8-37); Gly$^{8}$Arg$^{26,34}$Lys$^{36}$-GLP-1(8-37); Gly$^{8}$Arg$^{26}$-GLP-1(8-38); Gly$^{8}$Arg$^{34}$-GLP-1(8-38); Gly$^{8}$Arg$^{26,34}$Lys$^{38}$GLP-1(8-38); Gly$^{8}$Arg$^{26}$-GLP-1(8-39); Gly$^{8}$Arg$^{34}$-GLP-1(8-39); Gly$^{8}$Arg$^{26,34}$Lys$^{39}$-GLP-1(8-39); Val$^{8}$Arg$^{26}$-GLP-1(8-36); Val$^{8}$Arg$^{34}$-GLP-1(8-36); Val$^{8}$Arg$^{26,34}$Lye$^{36}$-GLP-1(8-36); Val$^{8}$Arg$^{26}$-GLP-1(8-36)amide; Val$^{8}$Arg$^{34}$-GLP-1(8-36)amide; Val$^{8}$Arg$^{26,34}$Lys$^{36}$-GLP-1(8-36)amide; Val$^{8}$Arg$^{26}$-GLP-1(8-37); Val$^{8}$Arg$^{34}$-GLP-1(8-37); Val$^{8}$Arg$^{26,34}$Lys$^{36}$-GLP-1(8-37); Val$^{8}$Arg$^{26}$-GLP-1(8-38); Val$^{8}$Arg$^{34}$-GLP-1(8-38); Val$^{8}$Arg$^{26,34}$Lys$^{38}$GLP-1(8-38); Val$^{8}$Arg$^{26}$-GLP-1(8-39); Val$^{8}$Arg$^{34}$-GLP-1(8-39); Val$^{8}$Arg$^{26,34}$Lys$^{39}$-GLP-1(8-39); Ser$^{8}$Arg$^{26}$-GLP-1(8-36); Ser$^{8}$Arg$^{34}$-GLP-1(8-36); Ser$^{8}$Arg$^{26,34}$Lys$^{36}$-GLP-1(8-36); Ser$^{8}$Arg$^{26}$-GLP-1(8-36)amide; Ser$^{8}$Arg$^{34}$-GLP-1(8-36)amide; Ser$^{8}$Arg$^{26,34}$Lys$^{36}$-GLP-1(8-36)amide; Ser$^{8}$Arg$^{26}$-GLP-1(8-37); Ser$^{8}$Arg$^{34}$-GLP-1(8-37); Ser$^{8}$Arg$^{26,34}$Lys$^{36}$-GLP-1(8-37); Ser$^{8}$Arg$^{26}$-GLP-1(8-38); Ser$^{8}$Arg$^{34}$-GLP-1(8-38); Ser$^{8}$Arg$^{26,34}$Lys$^{38}$GLP-1(8-38); Ser$^{8}$Arg$^{26}$-GLP-1(8-39); Ser$^{8}$Arg$^{34}$-GLP-1(8-39); Ser$^{8}$Arg$^{26,34}$Lys$^{39}$-GLP-1(8-39); Thr$^{8}$Arg$^{26}$-GLP-1(8-36); Thr$^{8}$Arg$^{34}$-GLP-1(8-36); Thr$^{8}$Arg$^{26,34}$Lys$^{36}$-GLP-1(8-36); Thr$^{8}$Arg$^{26}$-GLP-1(8-36)amide; Thr$^{8}$Arg$^{34}$-GLP-1(8-36)amide; Thr$^{8}$Arg$^{26,34}$Lys$^{36}$-GLP-1(8-36)amide; Thr$^{8}$Arg$^{26}$-GLP-1(8-37); Thr$^{8}$Arg$^{34}$-GLP-1(8-37); Thr$^{8}$Arg$^{26,34}$Lys$^{36}$-GLP-1(8-37); Thr$^{8}$Arg$^{26}$-GLP-1(8-38); Thr$^{8}$Arg$^{34}$-GLP-1(8-38); Thr$^{8}$Arg$^{26,34}$Lys$^{38}$GLP-1(8-38); Thr$^{8}$Arg$^{26}$-GLP-1(8-39); Thr$^{8}$Arg$^{34}$-GLP-1(8-39); Thr$^{8}$Arg$^{26,34}$Lys$^{39}$-GLP-1(8-39); Val$^{8}$Glu$^{35}$Arg$^{26,34}$Lys$^{36}$-GLP-1(8-36); Val$^{8}$Glu$^{35}$Arg$^{26,34}$Lys$^{36}$-GLP-1(8-36)amide; Val$^{8}$Glu$^{36}$Arg$^{26,34}$Lys$^{37}$GLP-1(8-37); Val$^{8}$Glu$^{37}$Arg$^{26,34}$Lys$^{38}$GLP-1(8-38); Val$^{8}$Glu$^{38}$Arg$^{26,34}$Lys$^{39}$-GLP-1(8-39); Val$^{8}$Glu$^{35}$Arg$^{26,34}$Lys$^{36}$-GLP-1(8-36); Val$^{8}$Glu$^{35}$Arg$^{26,34}$Lys$^{36}$-GLP-1(8-36)amide; Val$^{8}$Glu$^{36}$Arg$^{26,34}$Lys$^{37}$GLP-1(8-37); Val$^{8}$Glu$^{37}$Arg$^{26,34}$Lys$^{38}$GLP-1(8-38); Val$^{8}$Glu$^{38}$Arg$^{26,34}$Lys$^{39}$-GLP-1(8-39); Val$^{8}$Asp$^{35}$Arg$^{26,34}$Lys$^{36}$-GLP-1(8-36); Val$^{8}$Asp$^{35}$Arg$^{26,34}$Lys$^{36}$-GLP-1(8-36)amide; Val$^{8}$Asp$^{36}$Arg$^{26,34}$Lys$^{37}$GLP-1(8-37); Val$^{8}$Asp$^{37}$Arg$^{26,34}$Lys$^{38}$GLP-1(8-38); Val$^{8}$Asp$^{38}$Arg$^{26,34}$Lys$^{39}$-GLP-1(8-39); Val$^{8}$Asp$^{35}$Arg$^{26,34}$Lys$^{36}$-GLP-1(8-36); Val$^{8}$Asp$^{35}$Arg$^{26,34}$Lys$^{36}$-GLP-1(8-36)amide; Val$^{8}$Asp$^{36}$Arg$^{26,34}$Lys$^{37}$GLP-1(8-37); Val$^{8}$Asp$^{37}$Arg$^{26,34}$Lys$^{38}$GLP-1(8-38); Val$^{8}$Asp$^{26,34}$Lys$^{39}$-GLP-1(8-39); Ser$^{8}$Glu$^{35}$Arg$^{26,34}$Lys$^{36}$-GLP-1(8-36); Ser$^{8}$Glu$^{35}$Arg$^{26,34}$Lys$^{36}$-GLP-1(8-36)amide; Ser$^{8}$Glu$^{36}$Arg$^{26,34}$Lys$^{37}$GLP-1(8-37); Ser$^{8}$Glu$^{37}$Arg$^{26,34}$Lys$^{38}$GLP-1(8-38); Ser$^{8}$Glu$^{38}$Arg$^{26,34}$Lys$^{39}$-GLP1(8-39); Ser$^{8}$Glu$^{35}$Arg$^{26,34}$Lys$^{36}$-GLP-1(8-36); Ser$^{8}$Glu$^{35}$Arg$^{26,34}$Lys$^{36}$GLP-1(8-36)amide; Ser$^{8}$Glu$^{36}$Arg$^{26,34}$Lys$^{37}$GLP-1(8-37); Ser$^{8}$Glu$^{37}$Arg$^{26,34}$Lys$^{38}$GLP-1(8-38); Ser$^{8}$Glu$^{38}$Arg$^{26,34}$Lys$^{39}$-GLP-1(8-39); Ser$^{8}$Asp$^{35}$Arg$^{26,34}$Lys$^{36}$-GLP-1(8-36); Ser$^{8}$Asp$^{35}$Arg$^{26,34}$Lys$^{36}$-GLP-1(8-36)amide; Ser$^{8}$Asp$^{36}$Arg$^{26,34}$Lys$^{37}$GLP-1(8-37); Ser$^{8}$Asp$^{37}$Arg$^{26,34}$Lys$^{38}$GLP-1(8-38); Ser$^{8}$Asp$^{38}$Arg$^{26,34}$Lys$^{39}$-GLP-1(8-39); Ser$^{8}$Asp$^{35}$Arg$^{26,34}$Lys$^{36}$-GLP-1(8-36); Ser$^{8}$Asp$^{35}$Arg$^{26,34}$Lys$^{36}$-GLP-1(8-36)amide; Ser$^{8}$Asp$^{36}$Arg$^{26,34}$Lys$^{37}$GLP-1(8-37); Ser$^{8}$Asp$^{37}$Arg$^{26,34}$Lys$^{38}$GLP-1(8-38); Ser$^{8}$Asp$^{38}$Arg$^{26,34}$Lys$^{39}$-GLP-1(8-39); Thr$^{8}$Glu$^{35}$Arg$^{26,34}$Lys$^{36}$-GLP-1(8-36); Thr$^{8}$Glu$^{35}$Arg$^{26,34}$Lys$^{38}$-GLP-1(8-36)amide; Thr$^{8}$Glu$^{36}$Arg$^{26,34}$Lys$^{37}$GLP-1(8-37); Thr$^{8}$Glu$^{37}$Arg$^{26,34}$Lys$^{8}$GLP-1(8-38); Thr$^{8}$Glu$^{38}$Arg$^{26,34}$Lys$^{39}$-GLP-1(8-39); Thr$^{8}$Glu$^{35}$Arg$^{26,34}$Lys$^{36}$-GLP-1(8-36); Thr$^{8}$Glu$^{35}$Arg$^{26,34}$Lys$^{36}$-GLP-1(8-36)amide; Thr$^{8}$Glu$^{36}$Arg$^{26,34}$Lys$^{37}$GLP-1(8-37); Thr$^{8}$Glu$^{37}$Arg$^{26,34}$Lys$^{38}$GLP-1(8-38); Thr$^{8}$Glu$^{38}$Arg$^{26,34}$Lys$^{39}$-GLP-1(8-39); Thr$^{8}$Asp$^{35}$Arg$^{26,34}$Lys$^{36}$-GLP-1(8-36); Thr$^{8}$Asp$^{35}$Arg$^{26,34}$Lys$^{36}$-GLP-1(8-36)amide; Thr$^{8}$Asp$^{36}$Arg$^{26,34}$Lys$^{37}$GLP-1(8-37); Thr$^{8}$Asp$^{37}$Arg$^{26,34}$Lys$^{38}$GLP-1(8-38); Thr$^{8}$Asp$^{38}$Arg$^{26,34}$Lys$^{39}$-GLP-1(8-39); Thr$^{8}$Asp$^{35}$Arg$^{26,34}$Lys$^{36}$-GLP-1(8-36); Thr$^{8}$Asp$^{35}$Arg$^{26,34}$Lys$^{36}$-GLP-1(8-36)amide; Thr$^{8}$Asp$^{36}$Arg$^{26,34}$Lys$^{37}$GLP-1(8-37); The$^{8}$Asp$^{37}$Arg$^{26,34}$Lys$^{38}$GLP-1(8-38); Thr$^{8}$Asp$^{38}$Arg$^{26,34}$Lys$^{39}$-GLP-1(8-39); Gly$^{8}$Glu$^{35}$Arg$^{26,34}$Lys$^{36}$-GLP-1(8-36); Gly$^{8}$Glu$^{35}$Arg$^{26,34}$Lys$^{36}$-GLP-1(8-36)amide; Gly$^{8}$Glu$^{36}$Arg$^{26,34}$Lys$^{37}$GLP-1(8-37); Gly$^{8}$Glu$^{37}$Arg$^{26,34}$Lys$^{38}$GLP-1(8-38); Gly$^{8}$Glu$^{38}$Arg$^{26,34}$Lys$^{39}$-GLP-1(8-39); Gly$^{8}$Glu$^{35}$Arg$^{26,34}$Lys$^{36}$-GLP-1(8-36); Gly$^{8}$Glu$^{35}$Arg$^{26,34}$Lys$^{36}$GLP-1(8-36)amide; Gly$^{8}$Glu$^{36}$Arg$^{26,34}$Lys$^{37}$GLP-1(8-37); Gly$^{8}$Glu$^{37}$Arg$^{26,34}$Lys$^{38}$GLP-1(8-38); Gly$^{8}$Glu$^{38}$Arg$^{26,34}$Lys$^{39}$-GLP-1(8-39); Gly$^{8}$Asp$^{35}$Arg$^{26,34}$Lys$^{36}$-GLP-1(8-36); Gly$^{8}$Asp$^{35}$Arg$^{26,34}$Lys$^{36}$-GLP-1(8-36)amide; Gly$^{8}$Asp$^{36}$Arg$^{26,34}$Lys$^{37}$GLP-1(8-37); Gly$^{8}$Asp$^{37}$Arg$^{26,34}$Lys$^{38}$GLP-1(8-38); Gly$^{8}$Asp$^{38}$Arg$^{26,34}$Lys$^{39}$-GLP-1(8-39); Gly$^{8}$Asp$^{35}$Arg$^{26,34}$Lys$^{36}$-GLP-1(8-36); Gly$^{8}$Asp$^{35}$Arg$^{26,34}$Lys$^{36}$-GLP-1(8-36)amide; Gly$^{8}$Asp$^{36}$Arg$^{26,34}$Lys$^{37}$GLP-1(8-37); Gly$^{8}$Asp$^{37}$Arg$^{26,34}$Lys$^{38}$GLP-1(8-38);

Gly⁸Asp³⁸Arg²⁶,³⁴Lys³⁹-GLP-1(8-39); Arg²⁶,³⁴Lys¹⁸-GLP-1(8-36); Arg²⁶,³⁴Lys¹⁸-GLP-1(8-36)amide; Arg²⁶,³⁴Lys¹⁸GLP-1(8-37); Arg²⁶,³⁴Lys¹⁸GLP-1(8-38); Gly⁸Asp¹⁹Arg²⁶,³⁴Lys¹⁸-GLP-1(8-36); Gly⁸Asp¹⁷Arg²⁶,³⁴Lys¹⁸-GLP-1(8-36); Gly⁸Asp¹⁹Arg²⁶,³⁴Lys¹⁸-GLP-1(8-36)amide; Gly⁸Asp¹⁷Arg²⁶,³⁴Lys¹⁸-GLP-1(8-36)amide; Gly⁸Asp¹⁹Arg²⁶,³⁴Lys¹⁸GLP-1(8-37); Gly⁸Asp¹⁹Arg²⁶,³⁴Lys¹⁸GLP-1(8-38); Gly⁸Asp¹⁷Arg²⁶,³⁴Lys¹⁸GLP-1(8-38); Arg²⁶,³⁴Lys²³-GLP-1(8-36); Arg²⁶,³⁴Lys²³-GLP-1(8-36)amide; Arg²⁶,³⁴Lys²³GLP-1(8-37); Arg²⁶,³⁴Lys²³GLP-1(8-38); Gly⁸Asp²⁴Arg²⁶,³⁴Lys²³-GLP-1(8-36); Gly⁸Asp²²Arg²⁴,³⁶Lys²³-GLP-1(8-36); Gly⁸Asp²⁴Arg²⁶,³⁴Lys²³-GLP-1(8-36)amide; Gly⁸Asp²²Arg²⁶,³⁴Lys²³-GLP-1(8-36)amide; Gly⁸Asp²⁴Arg²⁶,³⁴Lys²³GLP-1(8-37); Gly⁸Asp²⁴Arg²⁶,³⁴Lys²³GLP-1(8-38); Gly⁸Asp²²Arg²⁶,³⁴Lys²³GLP-1(8-38); Arg²⁶,³⁴Lys²⁷-GLP-1(8-36); Arg²⁶,³⁴Lys²⁷-GLP-1(8-36)amide; Arg²⁶,³⁴Lys²⁷GLP-1(8-37); Arg²⁶,³⁴Lys²⁷GLP-1(8-38); Gly⁸Asp²⁸Arg²⁶,³⁴Lys²⁷-GLP-1(8-36); Gly⁸Asp²⁶Arg²⁶,³⁴Lys²⁷-GLP-1(8-36); Gly⁸Asp²⁸Arg²⁶,³⁴Lys²⁷-GLP-1(8-36)amide; Gly⁸Asp²⁶Arg²⁶,³⁴Lys²⁷-GLP-1(8-36)amide; Gly⁸Asp²⁸Arg²⁶,³⁴Lys²⁷GLP-1(8-37); Gly⁸Asp²⁸Arg²⁶,³⁴Lys²⁷GLP-1(8-38); Gly⁸Asp²⁶Arg²⁶,³⁴Lys²⁷GLP-1(8-38); Arg²⁶,³⁴Lys¹⁸-GLP-1(8-36); Arg²⁶,³⁴Lys¹⁸-GLP-1(8-36)amide; Arg²⁶,³⁴Lys¹⁸GLP-1(8-37); Arg²⁶,³⁴Lys¹⁸GLP-1(8-38); Val⁸Asp¹⁹Arg²⁶,³⁴Lys¹⁸-GLP-1(8-36); Val⁸Asp¹⁷Arg²⁶,³⁴Lys¹⁸-GLP-1(8-36); Val⁸Asp¹⁹Arg²⁶,³⁴Lys¹⁸-GLP-1(8-36)amide; Val⁸Asp¹⁷Arg²⁶,³⁴Lys¹⁸-GLP-1(8-36)amide; Val⁸Asp¹⁹Arg²⁶,³⁴Lys¹⁸GLP-1(8-37); Val⁸Asp¹⁹Arg²⁶,³⁴Lys¹⁸GLP-1(8-38); Val⁸Asp¹⁷Arg²⁶,³⁴Lys¹⁸GLP-1(8-38); Arg²⁶,³⁴Lys²³-GLP-1(8-36); Arg²⁶,³⁴Lys²³-GLP-1(8-36)amide; Arg²⁶,³⁴Lys²³GLP-1(8-37); Arg²⁶,³⁴Lys²³GLP-1(8-38); Val⁸Asp²⁴Arg²⁶,³⁴Lys²³-GLP-1(8-36); Val⁸Asp²²Arg²⁶,³⁴Lys²³-GLP-1(8-36); Val⁸Asp²⁴Arg²⁶,³⁴Lys²³-GLP-1(8-36)amide; Val⁸Asp²²Arg²⁶,³⁴Lys²³-GLP-1(8-36)amide; Val⁸Asp²⁴Arg²⁶,²⁴Lys²³GLP-1(8-37); Val⁸Asp²⁴Arg²⁶,³⁴Lys²³GLP-1(8-38); Val⁸Asp²²Arg²⁶,³⁴Lys²³GLP-1(8-38); Arg²⁶,³⁴Lys²⁷-GLP-1(8-36); Arg²⁶,³⁴Lys²⁷-GLP-1(8-36)amide; Arg²⁶,³⁴Lys²⁷GLP-1(8-37); Arg²⁶,³⁴Lys²⁷GLP-1(8-38); Val⁸Asp²⁸Arg²⁶,³⁴Lys²⁷-GLP-1(8-36); Val⁸Asp²⁶Arg²⁶,³⁴Lys²⁷-GLP-1(8-36); Val⁸Asp²⁸Arg²⁶,³⁴Lys²⁷-GLP-1(8-36)amide; Val⁸Asp²⁶Arg²⁶,³⁴Lys²⁷-GLP-1(8-36)amide; Val⁸Asp²⁸Arg²⁶,³⁴Lys²⁷GLP-1(8-37); Val⁸Asp²⁸Arg²⁶,³⁴Lys²⁷GLP-1(8-38); Val⁸Asp²⁶Arg²⁶,³⁴Lys²⁷GLP-1(8-38); Arg²⁶,³⁴Lys¹⁸-GLP-1(8-36); Arg²⁶,³⁴Lys¹⁸-GLP-1(8-36)amide; Arg²⁶,³⁴Lys¹⁸GLP-1(8-37); Arg²⁶,³⁴Lys⁸GLP-1(8-38); Ser⁸Asp¹⁹Arg²⁶,³⁴Lys¹⁸-GLP-1(8-36); Ser⁸Asp¹⁷Arg²⁶,³⁴Lys¹⁸-GLP-1(8-36); Ser⁸Asp¹⁹Arg²⁶,³⁴Lys¹⁸-GLP-1(8-36)amide; Ser⁹Asp¹⁷Arg²⁶,³⁴Lys¹⁸-GLP-1(8-36)amide; Ser⁸Asp¹⁹Arg²⁶,³⁴Lys¹⁸GLP-1(8-37); Ser⁸Asp¹⁹Arg²⁶,³⁴Lys¹⁸GLP-1(8-38); Ser⁸Asp¹⁷Arg²⁶,³⁴Lys¹⁸GLP-1(8-38); Arg²⁶,³⁴Lys²³-GLP-1(8-36); Arg²⁶,³⁴Lys²³-GLP-1(8-36)amide; Arg²⁶,³⁴Lys²³GLP-1(8-37); Arg²⁶,³⁴Lys²³GLP-1(8-38); Ser⁸Asp²⁴Arg²⁶,³⁴Lys²³-GLP-1(8-36); Ser⁸Asp²²Arg²⁶,³⁴Lys²³-GLP-1(8-36); Ser⁸Asp²⁴Arg²⁶,³⁴Lys²³-GLP-1(8-36)amide; Ser⁸Asp²²Arg²⁶,³⁴Lys²³-GLP-1(8-36)amide; Ser⁸Asp²⁴Arg²⁶,³⁴Lys²³GLP-1(8-37); Ser⁸Asp²⁴Arg²⁶,³⁴Lys²³GLP-1(8-38); Ser⁸Asp²²Arg²⁶,³⁴Lys²³GLP-1(8-38); Arg²⁶,³⁴Lys²⁷-GLP-1(8-36); Arg²⁶,³⁴Lys²⁷-GLP-1(8-36)amide; Arg²⁶,³⁴Lys²⁷GLP-1(8-37); Arg²⁶,³⁴Lys²⁷GLP-1(8-38); Ser⁸Asp²⁸Arg²⁶,³⁴Lys²⁷-GLP-1(8-36); Ser⁸Asp²⁶Arg²⁶,³⁴Lys²⁷-GLP-1(8-36); Ser⁸Asp²⁸Arg²⁶,³⁴Lys²⁷-GLP-1(8-36)amide; Ser⁸Asp²⁶Arg²⁶,³⁴Lys²⁷-GLP-1(8-36)amide; Ser⁸Asp²⁸Arg²⁶,³⁴Lys²⁷GLP-1(8-37); Ser⁸Asp²⁸Arg²⁶,³⁴Lys²⁷GLP-1(8-38); Ser⁸Asp²⁶Arg²⁶,³⁴Lys²⁷GLP-1(8-38); Arg²⁶,³⁴Lys¹⁸-GLP-1(8-36); Arg²⁶,³⁴Lys¹⁸-GLP-1(8-36)amide; Arg²⁶,³⁴Lys¹⁸GLP-1(8-37); Arg²⁶,³⁴Lys¹⁸GLP-1(8-38); Thr⁸Asp¹⁹Arg²⁶,³⁴Lys¹⁸-GLP-1(8-36); Thr⁸Asp¹⁷Arg²⁶,³⁴Lys¹⁸-GLP-1(8-36); Thr⁸Asp¹⁹Arg²⁶,³⁴Lys¹⁸-GLP-1(8-36)amide; Thr⁸Asp¹⁷Arg²⁶,³⁴Lys¹⁸-GLP-1(8-36)amide; Thr⁸Asp¹⁹Arg²⁶,³⁴Lys¹⁸GLP-1(8-37); Thr⁸Asp¹⁹Arg²⁶,³⁴Lys¹⁸GLP-1(8-38); Thr⁸Asp¹⁷Arg²⁶,³⁴Lys¹⁸GLP-1(8-38); Arg²⁶,³⁴Lys²³-GLP-1(8-36); Arg²⁶,³⁴Lys²³-GLP-1(8-36)amide; Arg²⁶,³⁴Lys²³GLP-1(8-37); Arg²⁶,³⁴Lys²³GLP-1(8-38); Thr⁸Asp²⁴Arg²⁶,³⁴Lys²³-GLP-1(8-36); Thr⁸Asp²²Arg²⁶,³⁴Lys²³-GLP-1(8-36); Thr⁸Asp²⁴Arg²⁶,³⁴Lys²³-GLP-1(8-36)amide; Thr⁸Asp²²Arg²⁶,³⁴Lys²³-GLP-1(8-36)amide; Thr⁸Asp²⁴Arg²⁶,³⁴Lys²³GLP-1(8-37); Thr⁸Asp²⁴Arg²⁶,³⁴Lys²³GLP-1(8-38); Thr⁸Asp²²Arg²⁶,³⁴Lys²³GLP-1(8-38); Arg²⁶,³⁴Lys²⁷-GLP-1(8-36); Arg²⁶,³⁴Lys²⁷-GLP-1(8-36)amide; Arg²⁶,³⁴Lys²⁷GLP-1(8-37); Arg²⁶,³⁴Lys²⁷GLP1(8-38); Thr⁸Asp²⁸Arg²⁶,³⁴Lys²⁷-GLP-1(8-36); Thr⁸Asp²⁶Arg²⁶,³⁴Lys²⁷-GLP-1(8-36); Thr⁸Asp²⁸Arg²⁶,³⁴Lys²⁷-GLP-1(8-36)amide; Thr⁸Asp²⁶Arg²⁶,³⁴Lys²⁷-GLP-1(8-36)amide; Thr⁸Asp²⁸Arg²⁶,³⁴Lys²⁷GLP-1(8-37); Thr⁸Asp²⁸Arg²⁶,³⁴Lys²⁷GLP-1(8-38); Thr⁸Asp²⁶Arg²⁶,³⁴Lys²⁷GLP-1(8-38); Arg²⁶Lys³⁶-GLP-1(8-36); Arg³⁴Lys³⁶-GLP-1(8-36); Arg²⁶Lys³⁶-GLP-1(8-37); Arg³⁴Lys³⁶-GLP-1(8-37); Arg²⁶Lys³⁷-GLP-1(8-37); Arg³⁴Lys³⁷-GLP-1(8-37); Arg²⁶Lys³⁹-GLP-1(8-39); Arg³⁴Lys³⁹-GLP-1(8-39); Arg²⁶,³⁴Lys³⁶,³⁹GLP-1(8-39); Arg²⁶Lys¹⁸-GLP-1(8-36); Arg³⁴Lys¹⁸-GLP-1(8-36); Arg²⁶Lys¹⁸GLP-1(8-37); Arg³⁴Lys¹⁸GLP-1(8-37); Arg²⁶Lys¹⁸GLP-1(8-38); Arg³⁴Lys¹⁸GLP-1(8-38); Arg²⁶Lys¹⁸GLP-1(8-39); Arg³⁴Lys¹⁸GLP-1(8-39); Arg²⁶Lys²³-GLP-1(8-36); Arg³⁴Lys²³-GLP-1(8-36); Arg²⁶Lys²³GLP-1(8-37); Arg³⁴Lys²³GLP-1(8-37); Arg²⁶Lys²⁷GLP-1(8-38); Arg³⁴Lys²³GLP-1(8-38); Arg²⁶Lys²⁷GLP-1(8-39); Arg³⁴Lys²⁷GLP-1(8-39); Arg²⁶Lys²⁷-GLP-1(8-36); Arg³⁴Lys²⁷-GLP-1(8-36); Arg²⁶Lys²⁷GLP-1(8-37); Arg³⁴Lys²⁷GLP-1(8-37); Arg²⁶Lys²⁷GLP-1(8-38); Arg³⁴Lys²⁷GLP-1(8-38); Arg²⁶Lys²⁷GLP-1(8-39); Arg³⁴Lys²⁷GLP-1(8-39); Arg²⁶,³⁴Lys¹⁸,³⁶-GLP-1(8-36); Arg²⁶,³⁴Lys¹⁸GLP-1(8-37); Arg²⁶,³⁴Lys¹⁸,³⁷GLP-1(8-37); Arg²⁶,³⁴Lys¹⁸,³⁸GLP-1(8-38); Arg²⁶,³⁴Lys¹⁸,³⁹GLP-1(8-39); Arg²⁶,³⁴Lys²³,³⁶-GLP-1(8-36); Arg²⁶,³⁴Lys²³GLP-1(8-37); Arg²⁶,³⁴Lys²³,³⁷GLP-1(8-37); Arg²⁶,³⁴Lys²³,³⁸GLP-1(8-38); Arg²⁶,³⁴Lys²³,³⁹GLP-1(8-39); Arg²⁶,³⁴Lys²⁷,³⁶-GLP-1(8-36); Arg²⁶,³⁴Lys²⁷GLP-1(8-37); Arg²⁶,³⁴Lys²⁷,³⁷GLP-1(8-37); Arg²⁶,³⁴Lys²⁷,³⁸GLP-1(8-38); Arg²⁶,³⁴Lys²⁷,³⁹GLP-1(8—39); Gly⁸GLP-1(8-36); Gly⁸GLP-1(8-37); Gly⁸GLP-1(8-

38); Gly$^8$GLP-1(8-39); Gly$^8$Arg$^{26}$Lys$^{36}$-GLP-1(8-36); Gly$^8$Arg$^{34}$Lys$^{36}$-GLP-1(8-36); Gly$^8$Arg$^{26}$Lys$^{36}$-GLP-1(8-37); Gly$^8$Arg$^{34}$Lys$^{36}$-GLP-1(8-37); Gly$^8$Arg$^{26}$Lys$^{37}$-GLP-1(8-37); Gly$^8$Arg$^{34}$Lys$^{37}$-GLP-1(8-37); Gly$^8$Arg$^{26}$Lys$^{39}$-GLP-1(8-39); Gly$^8$Arg$^{34}$Lys$^{39}$-GLP-1(8-39); Gly$^8$Arg$^{26,34}$Lys$^{36,39}$-GLP-1(8-39); Gly$^8$Arg$^{26}$Lys$^{18}$-GLP-1(8-36); Gly$^8$Arg$^{34}$Lys$^{18}$-GLP-1(8-36); Gly$^8$Arg$^{26}$Lys$^{18}$GLP-1(8-37); Gly$^8$Arg$^{34}$Lys$^{18}$GLP-1(8-37); Gly$^8$Arg$^{26}$Lys$^{18}$GLP-1(8-38); Gly$^8$Arg$^{34}$Lys$^{18}$GLP-1(8-38); Gly$^8$Arg$^{26}$Lys$^{18}$GLP-1(8-39); Gly$^8$Arg$^{34}$Lys$^{18}$GLP-1(8-39); Gly$^8$Arg$^{26}$Lys$^{23}$-GLP-1(8-36); Gly$^8$Arg$^{34}$Lys$^{23}$-GLP-1(8-36); Gly$^8$Arg$^{26}$Lys$^{23}$-GLP-1(8-37); Gly$^8$Arg$^{34}$Lys$^{23}$GLP-1(8-37); Gly$^8$Arg$^{26}$Lys$^{23}$GLP-1(8-38); Gly$^8$Arg$^{34}$Lys$^{23}$GLP-1(8-38); Gly$^8$Arg$^{26}$Lys$^{23}$GLP-1(8-39); Gly$^8$Arg$^{34}$Lys$^{23}$GLP-1(8-39); Gly$^8$Arg$^{26}$Lys$^{27}$-GLP-1(8-36); Gly$^8$Arg$^{34}$Lys$^{27}$-GLP-1(8-36); Gly$^8$Arg$^{26}$Lys$^{27}$GLP-1(8-37); Gly$^8$Arg$^{34}$Lys$^{27}$GLP-1(8-37); Gly$^8$Arg$^{26}$Lys$^{27}$GLP-1(8-38); Gly$^8$Arg$^{34}$Lys$^{27}$GLP-1(8-38); Gly$^8$Arg$^{26}$Lys$^{27}$GLP-1(8-39); Gly$^8$Arg$^{34}$Lys$^{27}$GLP-1(8-39); Gly$^8$Arg$^{26,34}$Lys$^{18,36}$-GLP-1(8-36); Gly$^8$Arg$^{26,34}$Lys$^{18}$GLP-1(8-37); Gly$^8$Arg$^{26,34}$Lys$^{18,37}$GLP-1(8-37); Gly$^8$Arg$^{26,34}$Lys$^{18,38}$GLP-1(8-38); Gly$^8$Arg$^{26,34}$Lys$^{18,39}$GLP-1(8-39); Gly$^8$Arg$^{26,34}$Lys$^{23,36}$-GLP-1(8-36); Gly$^8$Arg$^{226,34}$Lys$^{23}$GLP-1(8-37); Gly$^8$Arg$^{26,34}$Lys$^{23,37}$GLP1(8-37); Gly$^8$Arg$^{26,34}$Lys$^{23,38}$GLP-1(8-38); Gly$^8$Arg$^{26,34}$Lys$^{23,39}$GLP-1(8-39); Gly$^8$Arg$^{26,34}$Lys$^{27,36}$-GLP-1(8-36); Gly$^8$Arg$^{26,34}$Lys$^{27}$GLP-1(8-37); Gly$^8$Arg$^{26,34}$Lys$^{27,37}$GLP-1(8-37); Gly$^8$Arg$^{26,34}$Lys$^{27,38}$GLP-1(8-38); Gly$^8$Arg$^{26,34}$Lys$^{27,39}$GLP-1(8-39); Val$^8$GLP-1(8-36); Val$^8$GLP-1(8-37); Val$^8$GLP-1(8-38); Val$^8$GLP-1(8-39) Val$^8$Arg$^{26}$Lys$^{36}$-GLP-1(8-36); Val$^8$Arg$^{34}$Lys$^{36}$-GLP-1(7-36); Val$^8$Arg$^{26}$Lys$^{36}$-GLP-1(8-37); Val$^8$Arg$^{34}$Lys$^{36}$-GLP-1(8-37); Val$^8$Arg$^{26}$Lys$^{37}$-GLP-1(8-37); Val$^8$Arg$^{34}$Lys$^{37}$-GLP-1(8-37); Val$^8$Arg$^{26}$Lys$^{39}$-GLP-1(8-39); Val$^8$Arg$^{34}$Lys$^{39}$-GLP-1(8-39); Val$^8$Arg$^{26,34}$Lys$^{36,39}$-GLP-1(8-39); Val$^8$Arg$^{26}$Lys$^{18}$-GLP-1(8-36); Val$^8$Arg$^{34}$Lys$^{18}$-GLP-1(8-36); Val$^8$Arg$^{26}$Lys$^{18}$GLP-1(8-37); Val$^8$Arg$^{34}$Lys$^{18}$GLP-1(8-37); Val$^8$Arg$^{26}$Lys$^{18}$GLP-1(8-38); Val$^8$Arg$^{34}$Lys$^{18}$GLP-1(8-38); Val$^8$Arg$^{26}$Lys$^{18}$GLP-1(8-39); Val$^8$Arg$^{34}$Lys$^{18}$GLP-1(8-39); Val$^8$Arg$^{26}$Lys$^{23}$-GLP-1(8-36); Val$^8$Arg$^{34}$Lys$^{23}$-GLP-1(8-36); Val$^8$Arg$^{26}$Lys$^{23}$GLP-1(8-37); Val$^8$Arg$^{34}$Lys$^{23}$GLP-1(8-37); Val$^8$Arg$^{26}$Lys$^{23}$GLP-1(8-38); Val$^8$Arg$^{34}$Lys$^{23}$GLP-1(8-38); Val$^8$Arg$^{26}$Lys$^{23}$GLP-1(8-39); Val$^8$Arg$^{34}$Lys$^{23}$GLP-1(8-39); Val$^8$Arg$^{26}$Lys$^{27}$-GLP-1(8-36); Val$^8$Arg$^{34}$Lys$^{27}$-GLP-1(8-36); Val$^8$Arg$^{26}$Lys$^{27}$GLP-1(8-37); Val$^8$Arg$^{34}$Lys$^{27}$GLP-1(8-37); Val$^8$Arg$^{26}$Lys$^{27}$GLP-1(8-38); Val$^8$Arg$^{34}$Lys$^{27}$GLP-1(8-38); Val$^8$Arg$^{26}$Lys$^{27}$GLP-1(8-39); Val$^8$Arg$^{34}$Lys$^{27}$GLP-1(8-39); Val$^8$Arg$^{26,34}$Lys$^{18,36}$-GLP-1(8-36); Val$^8$Arg$^{26,34}$Lys$^{18}$GLP-1(8-37); Val$^8$Arg$^{26,34}$Lys$^{18,37}$GLP-1(8-37); Val$^8$Arg$^{26,34}$Lys$^{18,38}$GLP-1(8-38); Val$^8$Arg$^{26,34}$Lys$^{18,39}$GLP-1(8-39); Val$^8$Arg$^{26,34}$Lys$^{23,36}$-GLP-1(8-36); Val$^8$Arg$^{26,34}$Lys$^{23}$GLP-1(8-37); Val$^8$Arg$^{26,34}$Lys$^{23,37}$GLP-1(8-37); Val$^8$Arg$^{26,34}$Lys$^{23,38}$GLP-1(8-38); Val$^8$Arg$^{26,34}$Lys$^{23,39}$GLP-1(8-39); Val$^8$Arg$^{26,34}$Lys$^{27,36}$-GLP-1(8-36); Val$^8$Arg$^{26,34}$Lys$^{27}$GLP-1(8-37); Val$^8$Arg$^{26,34}$Lys$^{27,37}$GLP-1(8-37); Val$^8$Arg$^{26,34}$Lys$^{27,38}$GLP-1(8-38); Val$^8$Arg$^{26,34}$Lys$^{27,39}$GLP-1(8-39); Val$^8$GLP-1(7-37); Thr$^8$GLP-1(7-37); Met$^8$GLP-1(7-37); Gly$^8$GLP-1(7-37); Val$^8$GLP-1(7-36)amide; Thr$^8$GLP-1(7-36)amide; Met$^8$GLP-1(7-36)amide; Gly$^8$GLP-1(7-36)amide; Lys$^{26}$(N$^\epsilon$-tetradecanoyl)-GLP-1(7-37); Lys$^{34}$(N$^\epsilon$-tetradecanoyl)-GLP-1(7-37); Lys$^{26,34}$-bis(N$^\epsilon$-tetradecanoyl)-GLP-1(7-37); Gly$^8$Lys$^{26}$(N$^\epsilon$-tetradecanoyl)-GLP-1(7-37); Gly$^8$Lys$^{34}$(N$^\epsilon$-tetradecanoyl)-GLP-1(7-37); Gly$^8$Lys$^{26,34}$-bis(N$^\epsilon$-tetradecanoyl)-GLP-1(7-37); Arg$^{26}$Lys$^{34}$(N$^\epsilon$-tetradecanoyl)-GLP-1(7-37); Lys$^{26}$(N$^\epsilon$-tetradecanoyl)-GLP-1(7-38); Lys$^{34}$(N$^\epsilon$-tetradecanoyl)-GLP-1(7-38); Lys$^{26,34}$-bis(N$^\epsilon$-tetradecanoyl)-GLP-1(7-38); Gly$^8$Lys$^{26}$(N$^\epsilon$-tetradecanoyl)-GLP-1(7-38); Gly$^8$Lys$^{34}$(N$^\epsilon$-tetradecanoyl)-GLP-1(7-38); Gly$^8$Lys$^{26,34}$-bis(N$^\epsilon$-tetradecanoyl)-GLP-1(7-38); Arg$^{26}$Lys$^{34}$(N$^\epsilon$-tetradecanoyl)-GLP-1(7-38); Lys$^{26}$(N$^\epsilon$-tetradecanoyl)-GLP-1(7-39); Lys$^{34}$(N$^\epsilon$-tetradecanoyl)-GLP-1(7-39); Lys$^{26,34}$-bis(N$^{68}$-tetradecanoyl)-GLP-1(7-39); Gly$^8$Lys$^{26}$(N$^\epsilon$-tetradecanoyl)-GLP-1(7-39); Gly$^8$Lys$^{34}$(N$^\epsilon$-tetradecanoyl)-GLP-1(7-39); Gly$^8$Lys$^{26,34}$-bis(N$^\epsilon$tetradecanoyl)-GLP-1(7-39); Arg$^{26}$Lys$^{34}$(N$^\epsilon$-tetradecanoyl)-GLP-1(7-39); Lys$^{26}$(N$^\epsilon$-tetradecanoyl)-GLP-1(7-40); Lys$^{34}$(N$^\epsilon$-tetradecanoyl)-GLP-1(7-40); Lys$^{26,34}$-bis(N$^\epsilon$-tetradecanoyl)-GLP-1(7-40); Gly$^8$Lys$^{26}$(N$^\epsilon$-tetradecanoyl)-GLP-1(7-40); Gly$^8$Lys$^{34}$(N$^\epsilon$-tetradecanoyl)-GLP-1(7-40); Gly$^8$Lys$^{26,34}$-bis(N$^\epsilon$-tetradecanoyl)-GLP-1(7-40); Arg$^{26}$Lys$^{34}$(N$^\epsilon$-tetradecanoyl)-GLP-1(7-40); Lys$^{26}$(N$^\epsilon$-tetradecanoyl)-GLP-1(7-36); Lys$^{34}$(N$^\epsilon$-tetradecanoyl)-GLP-1(7-36); Lys$^{26,34}$-bis(N$^\epsilon$-tetradecanoyl)-GLP-1(7-36); Gly$^8$Lys$^{26}$(N$^\epsilon$-tetradecanoyl)-GLP-1(7-36); Gly$^8$Lys$^{34}$(N$^\epsilon$-tetradecanoyl)-GLP-1(7-36); Gly$^8$Lys$^{26,34}$-bis(N$^\epsilon$-tetradecanoyl)-GLP-1(7-36); Arg$^{26}$Lys$^{34}$(N$^\epsilon$-tetradecanoyl)-GLP-1(7-36); Lys$^{26}$(N$^\epsilon$-tetradecanoyl)-GLP-1(7-35); Lys$^{34}$(N$^\epsilon$-tetradecanoyl)-GLP-1(7-35); Lys$^{26,34}$-bis(N$^\epsilon$-tetradecanoyl)-GLP-1(7-35); Gly$^8$Lys$^{26}$(N$^\epsilon$-tetradecanoyl)-GLP-1(7-35); Gly$^8$Lys$^{34}$(N$^\epsilon$-tetradecanoyl)-GLP-1(7-35); Gly$^8$Lys$^{26,34}$-bis(N$^\epsilon$-tetradecanoyl)-GLP-1(7-35); Arg$^{26}$Lys$^{34}$(N$^\epsilon$-tetradecanoyl)-GLP-1(7-35); Lys$^{26}$(N$^\epsilon$-tetradecanoyl)-GLP-1(7-36)amide; Lys$^{34}$(N$^\epsilon$-tetradecanoyl)-GLP-1(7-36)amide; Lys26,34-bis(N$^\epsilon$-tetradecanoyl)-GLP-1(7-36)amide; Gly$^8$Lys$^{26}$(N$^\epsilon$-tetradecanoyl)-GLP-1(7-36)amide; Gly$^8$Lys$^{34}$(N$^\epsilon$-tetradecanoyl)-GLP-1(7-36)amide; Gly$^8$Lys$^{26,34}$-bis(N$^\epsilon$-tetradecanoyl)-GLP-1(7-36)amide; Arg$^{26}$Lys$^{34}$(N$^\epsilon$-tetradecanoyl)-GLP-1(7-36)amide; Gly$^8$Arg$^{26}$Lys$^{34}$(N$^\epsilon$-tetradecanoyl)-GLP-1(7-37); Lys$^{26}$(N$^\epsilon$-tetradecanoyl)Arg$^{34}$-GLP-1(7-37); Gly$^8$Lys$^{26}$(N$^\epsilon$-tetradecanoyl)Arg$^{34}$-GLP-1(7-37); Arg$^{26,34}$Lys$^{36}$(N$^\epsilon$-tetradecanoyl)-GLP-1(7-37); Gly$^8$Arg$^{26,34}$Lys$^{36}$(N$^\epsilon$-tetradecanoyl)-GLP-1(7-37); Gly$^8$Arg$^{26}$Lys$^{34}$(N$^\epsilon$-tetradecanoyl)-GLP-1(7-38); Lys$^{26}$(N$^\epsilon$-tetradecanoyl)Arg$^{34}$-GLP-1(7-38); Gly$^8$Lys$^{26}$(N$^\epsilon$-tetradecanoyl)Arg$^{34}$-GLP-1(7-38); Arg$^{26,34}$Lys$^{36}$(N$^\epsilon$-tetradecanoyl)-GLP-1(7-38); Arg$^{26}$Lys$^{38}$(N$^\epsilon$-tetradecanoyl)-GLP-1(7-38); Gly$^8$Arg$^{26,34}$Lys$^{36}$(N$^\epsilon$-tetradecanoyl)-GLP-1(7-38); Gly$^8$Arg$^{26}$Lys$^{34}$(N$^\epsilon$-tetradecanoyl)-GLP-1(7-39); Lys$^{26}$(N$^\epsilon$-tetradecanoyl)Arg$^{34}$-GLP-1(7-39); Gly$^8$Lys$^{26}$(N$^\epsilon$-tetradecanoyl)Arg$^{34}$-GLP-1(7-39); Arg$^{26,34}$Lys$^{36}$(N$^\epsilon$-tetradecanoyl)-GLP-1(7-39); Gly$^8$Arg$^{26,34}$Lys$^{36}$(N$^\epsilon$-tetradecanoyl)-GLP-1(7-39); Gly$^8$Arg$^{26}$Lys$^{34}$(N$^\epsilon$-tetradecanoyl)-GLP-1(7-40); Lys$^{26}$(N$^\epsilon$-tetradecanoyl)Arg$^{34}$-GLP-1(7-40); Gly$^8$Lys$^{26}$(N$^\epsilon$-tetradecanoyl)Arg$^{34}$-GLP-1(7-40); Arg$^{34}$Lys$^{36}$(N$^\epsilon$-tetradecanoyl)-GLP-1(7-40); Gly$^8$Arg$^{26}$Lys$^{34}$(N$^\epsilon$-tetradecanoyl)-GLP-1(7-40); Lys$^{26}$(N$^\epsilon$-($\omega$-carboxynonadecanoyl))-GLP-1(7-37); Lys$^{34}$(N$^{68}$-($\omega$-carboxynonadecanoyl))-GLP-1(7-37); Lys$^{26,34}$-bis(N$^\epsilon$-($\omega$-carboxynonadecanoyl))-GLP-1(7-37); Gly$^8$Lys$^{26}$(N$^\epsilon$-($\omega$-carboxynonadecanoyl))-GLP-1(7-37); Gly$^8$Lys$^{34}$(N$^\epsilon$-($\omega$-carboxynonadecanoyl))-GLP-1(7-37); Gly$^8$Lys$^{26,34}$-bis(N$^\epsilon$-($\omega$-carboxynonadecanoyl))-GLP-1(7-37); Lys$^{26}$(N$^\epsilon$-($\omega$-carboxynonadecanoyl))-GLP-1(7-38); Lys$^{34}$(N$^\epsilon$-($\omega$-carboxynonadecanoyl))-GLP-1(7-38); Lys$^{26,34}$-bis(N$^\epsilon$-($\omega$-carboxynonadecanoyl))-GLP-1(7-38); Gly$^8$Lys$^{26}$(N$^\epsilon$-($\omega$- carboxynonadecanoyl))-GLP-1(7-38); Gly$^8$Lys$^{34}$(N$^\epsilon$-(ω-carboxynonadecanoyl))-GLP-1(7-38); Gly$^8$Lys$^{26,34}$-bis(N$^\epsilon$-(ω-carboxynonadecanoyl))-GLP-1(7-38); Lys$^{26}$(N$^\epsilon$-(ω-carboxynonadecanoyl))-GLP-1(7-39); Lys$^{34}$(N$^\epsilon$-(ω-carboxynonadecanoyl))-GLP-1(7-39); Lys$^{26,34}$-bis(N$^\epsilon$-(ω-carboxynonadecanoyl))-GLP-1(7-39); Gly$^8$Lys$^{26}$(N$^\epsilon$-(ω-carboxynonadecanoyl))-GLP-1(7-39); Gly$^8$Lys$^{26}$(N$^\epsilon$-(ω-carboxynonadecanoyl))-GLP-1(7-39); Gly$^8$Lys$^{26,34}$-bis(N$^\epsilon$-(ω-carboxynonadecanoyl))-GLP-1(7-39); Lys$^{26}$(N$^\epsilon$-(ω-carboxynonadecanoyl))-GLP-1(7-40); Lys$^{34}$(N$^\epsilon$-(ω-carboxynonadecanoyl))-GLP-1(7-40); Lys$^{26,34}$-bis(N$^\epsilon$-(ω-carboxynonadecanoyl))-GLP-1(7-40); Gly$^8$Lys$^{26}$(N$^\epsilon$-(ω-carboxynonadecanoyl))-GLP-1(7-40); Gly$^8$Lys$^{34}$(N$^\epsilon$-(ω-carboxynonadecanoyl))-GLP-1(7-40); Gly$^8$Lys$^{26,34}$-bis(N$^\epsilon$-(ω-carboxynonadecanoyl))-GLP-1(7-40); Lys$^{26}$(N$^\epsilon$-(ω-carboxynonadecanoyl))-GLP-1(7-36); Lys$^{34}$(N$^\epsilon$-(ω-carboxynonadecanoyl))-GLP-1(7-36); Lys$^{26,34}$-bis(N$^\epsilon$-(ω-carboxynonadecanoyl))-GLP-1(7-36); Gly$^8$Lys$^{26}$(N$^\epsilon$-(ω-carboxynonadecanoyl))-GLP-1(7-36); Gly$^8$Lys$^{34}$(N$^\epsilon$-(ω-carboxynonadecanoyl))-GLP-1(7-36); Gly$^8$Lys$^{26,34}$-bis(N$^\epsilon$-(ω-carboxynonadecanoyl))-GLP-1(7-36); Lys$^{26}$(N$^\epsilon$-(ω-carboxynonadecanoyl))-GLP-1(7-36)amide; Lys$^{34}$(N$^\epsilon$-(ω-carboxynonadecanoyl))-GLP-1(7-36)amide; Lys$^{26,34}$-bis(N$^\epsilon$-(ω-carboxynonadecanoyl))-GLP-1(7-36)amide; Gly$^8$Lys$^{26}$(N$^\epsilon$-(ω-carboxynonadecanoyl))-GLP-1(7-36)amide; Gly$^8$Lys$^{34}$(N$^\epsilon$-(ω-carboxynonadecanoyl))-GLP-1(7-36)amide; Gly$^8$Lys$^{26,34}$-bis(N$^\epsilon$-(ω-carboxynonadecanoyl))-GLP-1(7-36)amide; Lys$^{26}$(N$^\epsilon$-(ω-carboxynonadecanoyl))-GLP-1(7-35); Lys$^{34}$(N$^\epsilon$-(ω-carboxynonadecanoyl))-GLP-1(7-35); Lys$^{26,34}$-bis(N$^\epsilon$-(ω-carboxynonadecanoyl))-GLP-1(7-35); Gly$^8$Lys$^{26}$(N$^\epsilon$-(ω-carboxynonadecanoyl))-GLP-1(7-35); Gly$^8$Lys$^{34}$(N$^\epsilon$-(ω-carboxynonadecanoyl))-GLP-1(7-35); Gly$^8$Lys$^{26,34}$-bis(N$^\epsilon$-(ω-carboxynonadecanoyl))-GLP-1(7-35); Arg$^{26}$Lys$^{34}$(N$^\epsilon$-(ω-carboxynonadecanoyl))-GLP-1(7-37); Gly$^8$Arg$^{26}$Lys$^{34}$(N$^\epsilon$-(ω-carboxynonadecanoyl))-GLP-1(7-37); Lys$^{26}$(N$^\epsilon$-(ω-carboxynonadecanoyl))Arg$^{34}$-GLP-1(7-37); Gly$^8$Lys$^{26}$(N$^\epsilon$-(ω-carboxynonadecanoyl))Arg$^{34}$-GLP-1(7-37); Arg$^{26,34}$Lys$^{36}$(N$^\epsilon$-(ω-carboxynonadecanoyl))-GLP-1(7-37); Gly$^8$Arg$^{26,34}$Lys$^{36}$(N$^\epsilon$-(ω-carboxynonadecanoyl))-GLP-1(7-38); Arg$^{26}$Lys$^{34}$(N$^\epsilon$-(ω-carboxynonadecanoyl))-GLP-1(7-38); Gly$^8$Arg$^{26}$Lys$^{34}$(N$^\epsilon$-(ω-carboxynonadecanoyl))-GLP-1(7-38); Lys$^{26}$(N$^\epsilon$-(ω-carboxynonadecanoyl))Arg$^{34}$-GLP-1(7-38); Gly$^8$Lys$^{26}$(N$^\epsilon$-(ω-carboxynonadecanoyl))Arg$^{34}$-GLP-1(7-38); Arg$^{26,34}$Lys$^{36}$(N$^\epsilon$-(ω-carboxynonadecanoyl))-GLP-1(7-38); Arg$^{26,34}$Lys$^{38}$(N$^\epsilon$-(ω-carboxynonadecanoyl))-GLP-1(7-38); Gly$^8$Arg$^{26,34}$Lys$^{36}$(N$^\epsilon$-(ω-carboxynonadecanoyl))-GLP-1(7-38); Arg$^{26}$Lys$^{34}$(N$^\epsilon$-(ε-carboxynonadecanoyl))-GLP-1(7-39); Gly$^8$Arg$^{26}$Lys$^{34}$(N$^\epsilon$-(ω-carboxynonadecanoyl))-GLP-1(7-39); Lys$^{26}$(N$^\epsilon$-(ω-carboxynonadecanoyl))Arg$^{34}$-GLP-1(7-39); Gly$^8$Lys$^{26}$(N$^\epsilon$-(ω-carboxynonadecanoyl))Arg$^{34}$-GLP-1(7-39); Arg$^{26,34}$Lys$^{36}$(N$^\epsilon$-(ω-carboxynonadecanoyl))-GLP-1(7-39); Gly$^8$Arg$^{26,34}$Lys$^{36}$(N$^\epsilon$-(ω-carboxynonadecanoyl))-GLP-1(7-39); Arg$^{34}$Lys$^{26}$(N$^\epsilon$-(γ-glutamyl(N$^\alpha$-hexadecanoyl)))-GLP-1(7-39)-OH Lys$^{26,34}$-bis(N$^\epsilon$-(γ-glutamyl(N$^\alpha$-hexadecanoyl)))-GLP-1(7-37)-OH, Lys$^{26,34}$-bis(N$^\epsilon$-(γ-glutamyl(N$^\alpha$-hexadecanoyl)))-GLP-1(7-37)-OH, Arg$^{26,34}$Lys$^{38}$(N$^\epsilon$-(γ-glutamyl(N$^\alpha$-tetradecanoyl)))-GLP-1(7-38)-OH, Arg$^{26,34}$Lys$^{38}$(N$^\epsilon$-(γ-glutamyl(N$^\alpha$-hexadecanoyl)))-GLP-1(7-38)-OH, Arg$^{26}$Lys$^{34}$(N$^\epsilon$-(ω-carboxynonadecanoyl))-GLP-1(7-40); Gly$^8$Arg$^{26}$Lys$^{34}$(N$^\epsilon$-(ω-carboxynonadecanoyl))-GLP-1(7-40); Lys$^{26}$(N$^\epsilon$-(ω-carboxynonadecanoyl))Arg$^{34}$-GLP-1(7-40); Gly$^8$Lys$^{26}$(N$^\epsilon$-(ω-carboxynonadecanoyl))Arg$^{34}$-GLP-1(7-40); Arg$^{26,34}$Lys$^{36}$(N$^\epsilon$-(ω-carboxynonadecanoyl))-GLP-1(7-40); Gly$^8$Arg$^{26,34}$Lys$^{36}$(N$^\epsilon$-(ω-carboxynonadecanoyl))-GLP-1(7-40); Lys$^{26}$(N$^\epsilon$-(7-deoxycholoyl))-GLP-1(7-37); Lys$^{34}$(N$^\epsilon$-(7-deoxycholoyl))-GLP-1(7-37); Lys$^{26,34}$-bis(N$^\epsilon$-(7-deoxycholoyl))-GLP-1(7-37); Gly$^8$Lys$^{26}$(N$^\epsilon$-(7-deoxycholoyl))-GLP-1(7-37); Gly$^8$Lys$^{34}$(N$^\epsilon$-(7-deoxycholoyl))-GLP-1(7-37); Gly$^8$Lys$^{26,34}$-bis(N$^\epsilon$-(7-deoxycholoyl))-GLP-1(7-37); Arg$^{26}$Lys$^{34}$(N$^\epsilon$-(7-deoxycholoyl))-GLP-1(7-37); Lys$^{26}$(N$^\epsilon$-(7-deoxycholoyl))-GLP-1(7-38); Lys$^{34}$(N$^\epsilon$-(7-deoxycholoyl))-GLP-1(7-38); Lys$^{26,34}$-bis(N$^\epsilon$-(7-deoxycholoyl))-GLP-1(7-38); Gly$^8$Lys$^{26}$(N$^\epsilon$-(7-deoxycholoyl))-GLP-1(7-38); Gly$^8$Lys$^{34}$(N$^\epsilon$-(7-deoxycholoyl))-GLP-1(7-38); Gly$^8$Lys$^{26,34}$-bis(N$^\epsilon$-(7-deoxycholoyl))-GLP-1(7-38); Arg$^{26}$Lys$^{34}$(N$^\epsilon$-(7-deoxycholoyl))-GLP-1(7-38); Lys$^{26}$(N$^\epsilon$-(7-deoxycholoyl))-GLP-1(7-39); Lys$^{34}$(N$^\epsilon$-(7-deoxycholoyl))-GLP-1(7-39); Lys$^{26,34}$-bis(N$^\epsilon$-(7-deoxycholoyl))-GLP-1(7-39); Gly$^8$Lys$^{26}$(N$^\epsilon$-(7deoxycholoyl))-GLP-1(7-39); Gly$^8$Lys$^{34}$(N$^\epsilon$-(7-deoxycholoyl))-GLP-1(7-39); Gly$^8$Lys$^{26,34}$-bis(N$^\epsilon$-(7-deoxycholoyl))-GLP-1(7-39); Arg$^{26}$Lys$^{34}$(N$^\epsilon$(7-deoxycholoyl))-GLP-1(7-39); Lys$^{26}$(N$^\epsilon$-(7-deoxycholoyl))-GLP-1(7-40); Lys$^{34}$(N$^\epsilon$-(7-deoxycholoyl))-GLP-1(7-40); Lys$^{26,34}$-bis(N$^\epsilon$-(7-deoxycholoyl))-GLP-1(7-40); Gly$^8$Lys$^{26}$(N$^\epsilon$-(7-deoxycholoyl))-GLP-1(7-40); Gly$^8$Lys$^{34}$(N$^\epsilon$-(7-deoxycholoyl))-GLP-1(7-40); Gly$^8$Lys$^{26}$(N$^\epsilon$-(7-deoxycholoyl))-GLP-1(7-40); Gly$^8$Lys$^{26,34}$-bis(N$^\epsilon$(7-deoxycholoyl))-GLP-1(7-40); Arg$^{26}$Lys$^{34}$(N$^\epsilon$-(7-deoxycholoyl))-GLP-1(7-40); Lys$^{26}$(N$^\epsilon$-(7-deoxycholoyl))-GLP-1(7-36); Lys$^{34}$(N$^\epsilon$-(7-deoxycholoyl))-GLP-1(7-36); Lys$^{26,34}$-bis(N$^\epsilon$-(7-deoxycholoyl))-GLP-1(7-36); Gly$^8$Lys$^{26}$(N$^\epsilon$-(7-deoxycholoyl))-GLP-1(7-36); Gly$^8$Lys$^{34}$(N$^\epsilon$-(7-deoxycholoyl))-GLP-1(7-36); Gly$^8$Lys$^{26}$ 34-bis(N$^\epsilon$-(7-deoxycholoyl))-GLP-1(7-36); Arg$^{26}$Lys$^{34}$(N$^\epsilon$-(7-deoxycholoyl))-GLP-1(7-36); Lys$^{26}$(N$^\epsilon$-(7-deoxycholoyl))-GLP-1(7-35); Lys$^{34}$(N$^\epsilon$-(7-deoxycholoyl))-GLP-1(7-35); Lys$^{26,34}$-bis(N$^\epsilon$-(7-deoxycholoyl))-GLP-1(7-35); Gly$^8$Lys$^{26}$(N$^\epsilon$-(7-deoxycholoyl))-GLP-1(7-35); Gly$^8$Lys$^{34}$(N$^\epsilon$-(7-deoxycholoyl))-GLP-1(7-35); Gly$^8$Lys$^{26,34}$-bis(N$^\epsilon$-(7-deoxycholoyl))-GLP-1(7-35); Arg$^{26}$Lys$^{34}$(N$^\epsilon$-(7-deoxycholoyl))-GLP-1(7-35); Lys$^{26}$(N$^\epsilon$-(7-deoxycholoyl))-GLP-1(7-36)amide; Lys$^{34}$(N$^\epsilon$-(7-deoxycholoyl))-GLP-1(7-36)amide; Lys$^{26,34}$-bis(N$^\epsilon$-(7-deoxycholoyl))-GLP-1(7-36)amide; Gly$^8$Lys$^{26}$(N$^\epsilon$-(7-deoxycholoyl))-GLP-1(7-36)amide; Gly$^8$Lys$^{34}$(N$^\epsilon$-(7-deoxycholoyl))-GLP-1(7-36)amide; Gly$^8$Lys$^{26,34}$-bis(N$^\epsilon$-(7-deoxycholoyl))-GLP-1(7-36)amide; Arg$^{26}$Lys$^{34}$(N$^\epsilon$-(7-deoxycholoyl))-GLP-1(7-36)amide; Gly$^8$Arg$^{26}$Lys$^{34}$(N$^\epsilon$-(7-deoxycholoyl))-GLP-1(7-36)amide; Lys$^{26}$(N$^\epsilon$-(7deoxycholoyl))Arg$^{34}$-GLP-1(7-37); Gly$^8$Lys$^{26}$((N$^\epsilon$-(7-deoxycholoyl))Arg$^{34}$-GLP-1(7-37); Arg$^{26,34}$Lys$^{36}$(N$^\epsilon$-(7-deoxycholoyl))-GLP-1(7-37); Gly$^8$Arg$^{26,34}$Lys$^{36}$(N$^\epsilon$-(7-deoxycholoyl))-GLP-1(7-37); Lys$^{26}$(N$^\epsilon$-(choloyl))-GLP-1(7-37); Lys$^{34}$(N$^\epsilon$-(choloyl))-GLP-1(7-37); Lys$^{26,34}$-bis(N$^\epsilon$-(choloyl))-GLP-1(7-37); Gly$^8$Lys26(N$^\epsilon$-(choloyl))-GLP-1(7-37); Gly$^8$Lys$^{34}$(N$^\epsilon$-(choloyl))-GLP-1(7-37); Gly$^8$Lys$^{26,34}$-bis(N$^\epsilon$-(choloyl))-GLP-1(7-37); Arg$^{26}$Lys$^{34}$(N$^\epsilon$-(choloyl))-GLP-1(7-37); Gly$^8$Arg$^{26}$Lys$^{34}$(N$^\epsilon$-(7-deoxycholoyl))-GLP-1(7-38); Lys$^{26}$(N$^\epsilon$-(7-deoxycholoyl))Arg$^{34}$-GLP-1(7-38); Gly$^8$Lys$^{26}$(N$^\epsilon$-(7-deoxycholoyl))Arg$^{34}$-GLP-1(7-38); Arg$^{26,34}$Lys$^{36}$(N$^\epsilon$-(7-deoxycholoyl))-GLP-1(7-38); Arg$^{26,34}$Lys$^{38}$(N$^\epsilon$-(7-deoxycholoyl))-GLP-1(7-38); Gly$^8$Arg$^{26,34}$Lys$^{36}$(N$^\epsilon$-(7-deoxycholoyl))-GLP-1(7-38); Lys$^{26}$(N$^\epsilon$-(choloyl))-GLP-1(7-38); Lys$^{34}$(N$^\epsilon$-(choloyl))-GLP-1(7-38); Lys$^{26,34}$-bis(N$^{68}$-(choloyl))-GLP-1(7-38); Gly$^8$Lys$^{26}$(N$^\epsilon$-(choloyl))-GLP-1(7-38); Gly$^8$Lys$^{34}$(N$^\epsilon$-(choloyl))-GLP-1(7-38); Gly$^8$Lys$^{26,34}$-bis(N$^\epsilon$-(choloyl))-GLP-1(7-38); Arg$^{26}$Lys$^{34}$(N$^\epsilon$-(choloyl))-GLP-1(7-38); Gly$^8$Arg$^{26}$Lys$^{34}$(N$^\epsilon$-(7-deoxycholoyl))-GLP-1(7-39); Lys$^{26}$(N$^\epsilon$-(7-deoxycholoyl))Arg$^{34}$-GLP-1(7-39); Gly$^8$Lys$^{26}$(N$^\epsilon$-(7-deoxycholoyl))

Arg³⁴-GLP-1(7-39); Arg²⁶,³⁴Lys³⁶(Nᵉ-(7-deoxycholoyl))-GLP-1(7-39); Gly⁸Arg²⁶,³⁴Lys³⁶(Nᵉ-(7-deoxycholoyl))-GLP-1(7-39); Lys²⁶(Nᵉ-(choloyl))-GLP-1(7-39); Lys³⁴(Nᵉ-(choloyl))-GLP-1(7-39); Lys²⁶,³⁴-bis(Nᵉ-(choloyl))-GLP-1(7-39); Gly⁸Lys²⁶(Nᵉ-(choloyl))-GLP-1(7-39); Gly⁸Lys³⁴(Nᵉ-(choloyl))GLP1(7-39); Gly⁸Lys²⁶,³⁴-bis(Nᵉ-(choloyl))-GLP-1(7-39); Arg²⁶Lys³⁴(Nᵉ-(choloyl))-GLP-1(7-39); Gly⁸Arg²⁶Lys³⁴(Nᵉ-(7-deoxycholoyl))-GLP-1(7-40); Lys²⁶(Nᵉ-(7-deoxycholoyl))Arg³⁴-GLP-1(7-40); Gly⁸Lys²⁶(Nᵉ-(7-deoxycholoyl))Arg³⁴-GLP-1(7-40); Arg²⁶,³⁴Lys³⁶(Nᵉ-(7-deoxycholoyl))-GLP-1(7-40); Gly⁸Arg²⁶,³⁴Lys³⁶(Nᵉ-(7-deoxycholoyl))-GLP-1(7-40); Lys²⁶(Nᵉ-(choloyl))-GLP-1(7-40); Lys³⁴(Nᵉ-(choloyl))-GLP-1(7-40); Lys²⁶,³⁴-bis(Nᵉ-(choloyl))-GLP-1(7-40); Gly⁸Lys²⁶(Nᵉ-(choloyl))-GLP-1(7-40); Gly⁸Lys³⁴(Nᵉ-(choloyl))-GLP-1(7-40); Gly⁸Lys²⁶,³⁴-bis(Nᵉ-(choloyl))-GLP-1(7-40); Arg²⁶Lys³⁴(Nᵉ-(choloyl))-GLP-1(7-40); Lys²⁶(Nᵉ-(choloyl))-GLP-1(7-36); Lys³⁴(Nᵉ-(choloyl))-GLP-1(7-36); Lys²⁶,³⁴-bis(Nᵉ-(choloyl))-GLP-1(7-36); Gly⁸Lys²⁶(Nᵉ-(choloyl))-GLP-1(7-36); Gly⁸Lys³⁴(Nᵉ-(choloyl))-GLP-1(7-36); Gly⁸Lys²⁶,³⁴-bis(Nᵉ-(choloyl))-GLP-1(7-36); Arg²⁶Lys³⁴(Nᵉ-(choloyl))-GLP-1(7-36); Lys²⁶(Nᵉ-(choloyl))-GLP-1(7-35); Lys³⁴(Nᵉ-(choloyl))-GLP-1(7-35); Lys²⁶,³⁴-bis(Nᵉ-(choloyl))-GLP-1(7-35); Gly⁸Lys²⁶(Nᵉ-(choloyl))-GLP-1(7-35); Gly⁸Lys³⁴(Nᵉ-(choloyl))-GLP-1(7-35); Gly⁸Lys²⁶,³⁴-bis(Nᵉ-(choloyl))-GLP-1(7-35); Arg²⁶Lys³⁴(Nᵉ-(choloyl))-GLP-1(7-35); Lys²⁶(Nᵉ-(choloyl))-GLP-1(7-36)amide; Lys³⁴(Nᵉ-(choloyl))-GLP-1(7-36)amide; Lys²⁶,³⁴-bis(Nᵉ-(choloyl))-GLP-1(7-36)amide; Gly⁸Lys²⁶(Nᵉ-(choloyl))-GLP-1(7-36)amide; Gly⁸Lys³⁴(Nᵉ-(choloyl))-GLP-1(7-36)amide; Gly⁸Lys²⁶,³⁴-bis(Nᵉ-(choloyl))-GLP-1(7-36)amide; Arg²⁶Lys³⁴(Nᵉ-(choloyl))-GLP-1(7-36)amide; Gly⁸Arg²⁶Lys³⁴(Nᵉ-(choloyl))-GLP-1(7-37); Lys²⁶(Nᵉ-(choloyl))Arg³⁴-GLP-1(7-37); Gly⁸Lys²⁶(Nᵉ-(choloyl))Arg³⁴-GLP-1(7-37); Arg²⁶,³⁴Lys³⁶(Nᵉ-(choloyl))-GLP-1(7-37); Gly⁸Arg²⁶,³⁴Lys⁶(Nᵉ-(choloyl))-GLP-1(7-37); Lys²⁶(Nᵉ-(lithocholoyl))-GLP-1(7-37); Lys³⁴(Nᵉ-(lithocholoyl))-GLP-1(7-37); Lys²⁶,³⁴-bis(Nᵉ-(lithocholoyl))-GLP-1(7-37); Gly⁸Lys²⁶(Nᵉ-(lithocholoyl))-GLP-1(7-37); Gly⁸Lys³⁴(Nᵉ-(lithocholoyl))-GLP-1(7-37); Gly⁸Lys²⁶,³⁴-bis(Nᵉ-(lithocholoyl))-GLP-1(7-37); Arg²⁶Lys³⁴(Nᵉ-(lithocholoyl))-GLP-1(7-37); Gly⁸Arg²⁶Lys³⁴(Nᵉ-(choloyl))-GLP-1(7-38); Lys²⁶(Nᵉ-(choloyl))Arg³⁴-GLP-1(7-38); Gly⁸Lys²⁶(Nᵉ-(choloyl))Arg³⁴-GLP-1(7-38); Arg²⁶,³⁴Lys³⁶(Nᵉ-(choloyl))-GLP-1(7-38); Arg²⁶,³⁴Lys³⁶(Nᵉ-(choloyl))-GLP-1(7-38); Gly⁸Arg²⁶,³⁴Lys³⁶(Nᵉ-(choloyl))-GLP-1(7-38); Lys²⁶(Nᵉ-(lithocholoyl))-GLP-1(7-38); Lys³⁴(Nᵉ-(lithocholoyl))-GLP-1(7-38); Lys²⁶,³⁴-bis(Nᵉ-(lithocholoyl))-GLP-1(7-38); Gly⁸Lys²⁶(Nᵉ-(lithocholoyl))-GLP-1(7-38); Gly⁸Lys³⁴(Nᵉ-(lithocholoyl))-GLP-1(7-38); Gly⁸Lys²⁶,³⁴-bis(Nᵉ-(lithocholoyl))-GLP-1(7-38); Arg²⁶Lys³⁴(Nᵉ-(lithocholoyl))-GLP-1(7-38); Gly⁸Arg²⁶Lys³⁴(Nᵉ-(choloyl))-GLP-1(7-39); Lys²⁶(Nᵉ-(choloyl))Arg³⁴-GLP-1(7-39); Gly⁸Lys²⁶(Nᵉ-(choloyl))Arg³⁴-GLP-1(7-39); Arg²⁶,³⁴Lys³⁶(Nᵉ-(choloyl))-GLP-1(7-39); Gly⁸Arg²⁶,³⁴Lys³⁶(Nᵉ-((choloyl))-GLP-1(7-39); Lys²⁶(Nᵉ-(lithocholoyl))-GLP-1(7-39); Lys³⁴(Nᵉ-(lithocholoyl))-GLP-1(7-39); Lys²⁶,³⁴-bis(Nᵉ-(lithocholoyl))-GLP-1(7-39); Gly⁸Lys²⁶(Nᵉ-(lithocholoyl))-GLP-1(7-39); Gly⁸Lys³⁴(Nᵉ-(lithocholoyl))-GLP-1(7-39); Gly⁸Lys²⁶,³⁴-bis(Nᵉ-(lithocholoyl))-GLP-1(7-39); Arg²⁶Lys³⁴(Nᵉ-(lithocholoyl))-GLP-1(7-39); Gly⁸Arg²⁶Lys³⁴(Nᵉ-(choloyl))-GLP-1(7-40); Lys²⁶(Nᵉ-(choloyl))Arg³⁴-GLP-1(7-40); Gly⁸Lys²⁶(Nᵉ-(choloyl))Arg³⁴-GLP-1(7-40); Arg²⁶,³⁴Lys³⁶(Nᵉ-(choloyl))-GLP-1(7-40); Gly⁸Arg²⁶,³⁴Lys³⁶(Nᵉ-(choloyl))-GLP-1(7-40); Lys²⁶(Nᵉ-(lithocholoyl))-GLP-1(7-40); Lys³⁴(Nᵉ-(lithocholoyl))-GLP-1(7-40); Lys²⁶,³⁴-bis(Nᵉ-(lithocholoyl))-GLP-1(7-40); Gly⁸Lys²⁶(Nᵉ-(lithocholoyl))-GLP-1(7-40); Gly⁸Lys³⁴(Nᵉ-(lithocholoyl))-GLP-1(7-40); Gly⁸Lys²⁶,³⁴-bis(Nᵉ-(lithocholoyl))-GLP-1(7-40); Arg²⁶Lys³⁴(Nᵉ-(lithocholoyl))-GLP-1(7-37); Lys²⁶(Nᵉ-(lithocholoyl))-GLP-1(7-36); Lys³⁴(Nᵉ-(lithocholoyl))-GLP-1(7-36); Lys²⁶,³⁴-bis(Nᵉ-(lithocholoyl))-GLP-1(7-36); Gly⁸Lys²⁶(Nᵉ-(lithocholoyl))-GLP-1(7-36); Gly⁸Lys³⁴(Nᵉ-(lithocholoyl))-GLP-1(7-36); Gly⁸Lys²⁶,³⁴-bis(Nᵉ-(lithocholoyl))-GLP-1(7-36); Arg²⁶Lys³⁴(Nᵉ-(lithocholoyl))-GLP-1(7-36); Lys²⁶(Nᵉ-(lithocholoyl))-GLP-1(7-35); Lys³⁴(Nᵉ-(lithocholoyl))-GLP-1(7-35); Lys²⁶,³⁴(Nᵉ-(lithocholoyl))-GLP-1(7-35); Gly⁸Lys²⁶-bis(Nᵉ-(lithocholoyl))-GLP-1(7-35); Gly⁸Lys³⁴(Nᵉ-(lithocholoyl))-GLP-1(7-35); Gly⁸Lys²⁶,³⁴(Nᵉ-(lithocholoyl))-GLP-1(7-35); Arg²⁶Lys³⁴(Nᵉ-(lithocholoyl))-GLP-1(7-35); Lys²⁶(Nᵉ-(lithocholoyl))-GLP-1(7-36)amide; Lys³⁴(Nᵉ-(lithocholoyl))-GLP-1(7-36)amide; Lys²⁶,³⁴-bis(Nᵉ-(lithocholoyl))-GLP-1(7-36)amide; Gly⁸Lys²⁶(Nᵉ-(lithocholoyl))-GLP-1(7-36)amide; Gly⁸Lys³⁴(Nᵉ-(lithocholoyl))-GLP-1(7-36)amide; Gly⁸Lys²⁶,³⁴-bis(Nᵉ-(lithocholoyl))-GLP-1(7-36)amide; Arg²⁶Lys³⁴(Nᵉ-(lithocholoyl))-GLP-1(7-36)amide; Gly⁸Arg²⁶Lys³⁴(Nᵉ-(lithocholoyl))-GLP-1(7-37); Lys²⁶(Nᵉ-(lithocholoyl))Arg³⁴GLP-1(7-37); Gly 8Lys²⁶(Nᵉ-(lithocholoyl))Arg³⁴-GLP-1(7-37); Arg²⁶,³⁴Lys³⁶(Nᵉ-(lithocholoyl))-GLP-1(7-37); Arg²⁶,³⁴Lys³⁸(Nᵉ-(lithocholoyl))-GLP-1(7-37); Gly⁸Arg²⁶,³⁴Lys³⁶(Nᵉ-(lithocholoyl))-GLP-1(7-37); Gly⁸Arg²⁶Lys³⁴(Nᵉ-(lithocholoyl))-GLP-1(7-38); Lys²⁶(Nᵉ-(lithocholoyl))Arg³⁴-GLP-1(7-38); Gly⁸Lys²⁶(Nᵉ-(lithocholoyl))Arg³⁴-GLP-1(7-38); Arg²⁶,³⁴Lys³⁶(Nᵉ-(lithocholoyl))-GLP-1(7-38); Arg²⁶,³⁴Lys³⁸(Nᵉ-(lithocholoyl))-GLP-1(7-38); Gly⁸Arg²⁶,³⁴Lys³⁶(Nᵉ-(lithocholoyl))-GLP-1(7-38); Gly⁸Arg²⁶Lys³⁴(Nᵉ-(lithocholoyl))-GLP-1(7-39); Lys²⁶(Nᵉ-(lithocholoyl))Arg³⁴-GLP-1(7-39); Gly⁸Lys²⁶(Nᵉ-(lithocholoyl))Arg³⁴-GLP-1(7-39); Arg²⁶,³⁴Lys³⁶(Nᵉ-(lithocholoyl))-GLP-1(7-39); Gly⁸Arg²⁶,³⁴Lys³⁶(Nᵉ-(lithocholoyl))-GLP-1(7-39); Gly⁸Arg²⁶Lys³⁴(Nᵉ-(lithocholoyl))-GLP-1(7-40); Lys²⁶(Nᵉ-(lithocholoyl)Arg³⁴-GLP-1(7-40); Gly⁸Lys²⁶(Nᵉ-(lithocholoyl)Arg³⁴-GLP-1(7-40); Arg²⁶,³⁴Lys³⁶(Nᵉ-(lithocholoyl))-GLP-1(7-40) and Gly⁸Arg²⁶,³⁴Lys³⁶(Nᵉ-(lithocholoyl))-GLP-1(7-40). Each of these GLP-1 peptides constitutes an alternative embodiment of the present invention.

In a further embodiment of the present invention the GLP-1 related impurities to be removed are selected from but not limited to truncated forms, all kinds of extended forms (extra amino acids, various derivatives including esters etc.), deamidated forms, incorrectly folded forms, forms with undesired glycosylation including sialylation. As an example illustrating the present invention, histidine has a predominant positive net charge below pH~6.5, thus for cation exchange the pH elution gradient with a solvent comprising an organic solvent or modifier could begin below pH 6.5 to remove a truncated form missing histidine and end the gradient above pH 6.5 thereby subsequently eluting the target GLP-1 moiety. As an alternative, the elution separating the truncated form from the target GLP-1 moiety employing organic modifier could be performed below pH 6.5 simply by a salt component (gradient or isocratically) at eluting conditions. As another alternative, the elution separating the truncated form from the target GLP-1 moiety employing organic modifier could be performed below pH 6.5 by a gradient in the organic modifier from a lower to a higher content. As a second example, the carboxyl group of the C-terminal amino acid has a predominant negative net charge above pH~3.1, thus for anion exchange the pH elution gradient with a solvent comprising an organic modifier could begin above pH 3.1 to remove a form extended to an amide and end the gradient below pH 3.1 thereby subsequently eluting the target GLP-1 moiety. Alternatively, the elution separating the amide form from the target GLP-1 moiety employing organic modifier could be performed above pH 3.1 simply by a salt component (gradient or isocratically) at eluting conditions. As a third example, aspartic acid has a predominant negative net charge above pH~4.4, thus for anion exchange the pH elution gradient with a solvent comprising an organic modifier could begin above pH 4.4 to remove a truncated form missing aspartic acid and end the gradient below pH 4.4 thereby subsequently eluting the target GLP-1 moiety. Alternatively, the elution separating the truncated form from the target GLP-1 moiety employing organic modifier could be performed above pH 4.4 simply by a salt component (gradient or isocratically) at eluting conditions. As a fourth example, glutamic acid has a predominant negative net charge above pH~4.4, thus for anion exchange the pH elution gradient with a solvent comprising an organic modifier could begin above pH 4.4 to elute the target GLP-1 moiety and end the gradient below pH 4.4 thereby subsequently removing an extended form comprising an extra glutamic acid residue. Alternatively, the elution separating the extended form from the target GLP-1 moiety employing organic modifier could be performed above pH 4.4 simply by a salt component (gradient or isocratically) at eluting conditions. As a fifth example, the amino group of the N-terminal amino acid has a predominant positive net charge below pH~8.0, thus for cation exchange the pH elution gradient with a solvent comprising an organic modifier could begin below pH 8.0 to remove a form extended with an undesired acyl group and end the gradient above pH 8.0 thereby subsequently eluting the target GLP-1 moiety. Alternatively, the elution separating the acylated form from the target GLP-1 moiety employing organic modifier could be performed below pH 8.0 simply by a salt component (gradient or isocratically) at eluting conditions. As a sixth example, the amino group of the N-terminal amino acid has a predominant positive net charge below pH~8.0, thus for cation exchange the pH elution gradient with a solvent comprising an organic modifier could begin below pH 8.0 to elute the target GLP-1 moiety which is extended with a desired acyl group and end the gradient above pH 8.0 thereby subsequently removing the undesired non-extended form. Alternatively, the elution separating the acylated target GLP-1 moiety from the non-acylated form employing organic modifier could be performed below pH 8.0 simply by a salt component (gradient or isocratically) at eluting conditions. As a seventh example, tyrosine has a predominant negative net charge above pH~10.0, thus for anion exchange the pH elution gradient with a solvent comprising an organic modifier could begin above pH 10.0 to remove a truncated form missing a tyrosine residue and end the gradient below pH 10.0 thereby subsequently eluting the target GLP-1 moiety. Alternatively, the elution separating the truncated form from the target GLP-1 moiety employing organic modifier could be performed above pH 10.0 simply by a salt component (gradient or isocratically) at eluting conditions. As an eighth example, lysine has a predominant positive net charge below pH~10.0, thus for cation exchange the pH elution gradient with a solvent comprising an organic modifier could begin below pH 10.0 to elute a target GLP-1 moiety acylated in the side chain of the lysine residue and end the gradient above pH 10.0 thereby subsequently removing an undesired non-acylated form. Alternatively, the elution separating the acylated target GLP-1 moiety from the non-acylated form employing organic modifier could be performed below pH 10.0 simply by a salt component (gradient or isocratically) at eluting conditions. As a ninth example, arginine has a predominant positive net charge below pH~12.0, thus for anion exchange the pH elution gradient with a solvent comprising an organic modifier could begin below pH 12.0 to elute the target GLP-1 moiety and end the gradient above pH 12.0 thereby subsequently removing an undesired form comprising an extra arginine residue. Alternatively, the elution separating the target GLP-1 moiety from the form comprising an extra arginine residue employing organic modifier could be performed below pH 12.0 simply by a salt component (gradient or isocratically) at eluting conditions. ($pK_A$-values used in these examples are from: L. Stryer. Biochemistry, $3^{rd}$ edition, W. H. Freeman and Company, New York, Table 2-1 page 21).

In a further embodiment of the present invention the impurities to be removed are not GLP-1 related.

Specific GLP-1 peptide examples of the above-mentioned method are separation of $Arg^{34}$GLP-1(7-37) and $Arg^{34}$GLP-1(9-37) by cation exchange chromatography, GLP-1(7-37) and GLP-1(7-36) amide by anion exchange chromatography, GLP-1(15-37) and GLP-1(16-37) by anion exchange chromatography, $Arg^{34}$GLP-1(7-37) and $Arg^{34}Lys^{26}(N^{\epsilon}$-Glu)GLP-1(7-37) by anion exchange chromatography, $Arg^{34}Lys^{26}(N^{\epsilon}$-($\gamma$-Glu-($N^{\alpha}$-tetradecanoyl)))GLP-1 (7-37) and $Arg^{34}Lys^{26}(N^{\epsilon}$-($\gamma$-Glu-(N$\alpha$-tetradecanoyl)))$Gly^{37}(N^{\alpha}$-($\gamma$-Glu-($N^{\alpha}$-tetradecanoyl))) GLP-1(7-37) by cation exchange chromatography, $Gly^{37}(N^{\epsilon}$-($\gamma$-Glu-($N^{\alpha}$-tetradecanoyl)))GLP-1(7-37) and GLP-1(7-37) by cation exchange chromatography, GLP-1(19-37) and GLP-1(20-37) by anion exchange chromatography, $Arg^{34}Lys^{26}(N^{\epsilon}$-($\gamma$-Glu-($N^{\alpha}$-tetradecanoyl)))GLP-1(7-37) and $Arg^{34}$GLP-1(7-37) by cation exchange chromatography, and GLP-1(7-37) and $Arg^{34}$GLP-1(7-37) by cation exchange chromatography employing salt and/or pH gradients.

In a further embodiment of the present invention the peptide to be purified is a GLP-2 peptide.

In a further embodiment of the present invention the peptide to be purified is selected from GLP-2(1-34), GLP-2(1-33) as well as analogues and derivatives thereof, in particular but not limited to human glucagon-like peptide-2(hGLP-2), GLP-2(1-30); GLP-2(1-31); GLP-2(1-32); GLP-2(1-33); GLP-2(1-34), GLP-2(1-35), $Lys^{20}$GLP-2(1-33), $Lys^{20}Arg^{30}$GLP-2(1-33), $Arg^{30}Lys^{34}$GLP-2(1-34), $Arg^{30}Lys^{35}$GLP-2(1-35), $Arg^{30,35}Lys^{20}$GLP-2(1-35), $Arg^{35}$GLP-2(1-35), $Lys^{20}(N^{\epsilon}$-tetradecanoyl)GLP-2(1-33); $Lys^{20,30}$-bis($N^{\epsilon}$-tetradecanoyl)GLP-2(1-33); $Lys^{20}(N^{\epsilon}$-tetradecanoyl)$Arg^{30}$GLP-2(1-33); $Arg^{30}Lys^{35}(N^{\epsilon}$-tetradecanoyl)GLP-2(1-35); $Arg^{30,35}Lys^{20}(N^{\epsilon}$-tetradecanoyl)GLP-2(1-35); $Arg^{35}Lys^{30}(N^{\epsilon}$-tetradecanoyl) GLP-2(1-35); $Arg^{30}Lys^{34}(N^{\epsilon}$-tetradecanoyl)GLP-2(1-34); $Lys^{20}(N^{\epsilon}$-($\omega$-carboxynonadecanoyl))GLP-2(1-33); $Lys^{20,30}$-bis($N^{\epsilon}$-($\omega$-carboxynonadecanoyl))GLP-2(1-33); $Lys^{20}(N^{\epsilon}$-($\omega$-carboxynonadecanoyl))$Arg^{30}$GLP-2(1-33); $Arg^{30}Lys^{35}$($N^{\epsilon}$-($\omega$-carboxynonadecanoyl))GLP-2(1-35); $Lys^{30}(N^{\epsilon}$-($\gamma$-glutamyl($N^{\alpha}$-tetradecanoyl)))hGLP-2, $Arg^{30,35}Lys^{20}(N^{\epsilon}$-($\omega$-carboxynonadecanoyl))GLP-2(1-35); $Arg^{35}Lys^{30}(N^{\epsilon}$-($\omega$-carboxynonadecanoyl))GLP-2(1-35); and $Arg^{30}Lys^{34}$($N^{\epsilon}$-($\omega$-carboxynonadecanoyl))GLP-2(1-34).

The peptides or GLP-1 peptides can be produced by a method which comprises culturing or fermenting a host cell containing a DNA sequence encoding the peptide or GLP-1 peptide and capable of expressing said peptide in a suitable nutrient medium under conditions permitting the expression of the peptide, after which the resulting peptide or GLP-1 peptide is recovered from the culture or fermentation broth. Hereinafter, culturing will be used to cover both culturing and fermenting and the like.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide or GLP-1 peptide produced by the cells may then be recovered from the culture medium by conventional procedures including, optionally lysis of cells, separating the host cells from the medium by centrifugation or filtration, precipitating the proteinaceous components of the supernatant or filtrate by means of a salt, e.g. ammonium sulphate, purification by conventional purification techniques, such as chromatographic techniques, if necessary, purification by ion exchange chromatography according to the present invention, and subsequently, subjecting to analytical tests, e.g. PAGE, IEF, if necessary, subjecting to further purification, if necessary, and isolation of the pure peptide or GLP-1 peptide.

During the recovery of the resulting peptide or GLP-1 peptide from the culture medium, but before purification by ion exchange chromatography according to the present invention, the mixture comprising the peptide or GLP-1 peptide and related impurities may optionally be chemically modified by conventional techniques, e.g. by alkylation, acylation, ester formation or amide formation or the like.

The DNA sequence encoding the parent peptide or GLP-1 peptide may suitably be of genomic or cDNA origin, for instance obtained by preparing a genomic or cDNA library and screening for DNA sequences coding for all or part of the peptide or GLP-1 peptide by hybridisation using synthetic oligonucleotide probes in accordance with standard techniques (see, for example, Sambrook, J, Fritsch, EF and Maniatis, T, *Molecular Cloning: A Laboratory Manual*, Cold Spring Harbor Laboratory Press, New York, 1989). The DNA sequence encoding the peptide or GLP-1 peptide may also be prepared synthetically by established standard methods, e.g. the phosphoamidite method described by Beaucage and Caruthers, *Tetrahedron Letters* 22 (1981), 1859–1869, or the method described by Matthes et al, *EMBO Journal* 3 (1984), 801–805. The DNA sequence may also be prepared by polymerase chain reaction using specific primers, for instance as described in U.S. Pat. No. 4,683,202 or Saiki et al, *Science* 239 (1988), 487–491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide or GLP-1 peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide or GLP-1 peptide of the invention in a variety of host cells are well known in the art, cf. for instance Sambrook et al., supra.

The DNA sequence encoding the peptide or GLP-1 peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a peptide or GLP-1 peptide into the secretory pathway of the host cells, a secretory signal sequence (also known as a leader sequence, prepro sequence or pre sequence) may be provided in the recombinant vector. The secretory signal sequence is joined to the DNA sequence encoding the GLP-1 peptide in the correct reading frame. Secretory signal sequences are commonly positioned 5' to the DNA sequence encoding the peptide or GLP-1 peptide. The secretory signal sequence may be that normally associated with the peptide or GLP-1 peptide or may be from a gene encoding another secreted protein.

The procedures used to ligate the DNA sequences coding for the peptide or GLP-1 peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide or GLP-1 peptide and includes bacteria, vira, e.g. baculo virus, yeast, fungi, insect cells and higher eukaryotic cells. Examples of suitable host cells well known and used in the art are, without limitation, *E coli, Saccharomyces cerevisiae*, or mammalian BHK or CHO cell lines.

Some of the peptides or GLP-1 peptides, can be produced according to conventional organic peptide synthetic chemistry. The resulting synthetic mixture may then be chemically modified, e.g. by alkylation, acylation, ester formation or amide formation or the like, and purified, or purified as it is and then modified chemically as mentioned above.

Preparation of Factor VIIa

Human purified factor VIIa suitable for use in the present invention is preferably made by DNA recombinant technology, e.g. as described by Hagen et al., *Proc.Natl.Acad.Sci. USA* 83: 2412–2416, 1986 or as described in European Patent No. 200.421 (ZymoGenetics). Factor VIIa produced by recombinant technology may be authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, *J.Biol.Chem.* 255 (4):

1242–1247, 1980 and Hedner and Kisiel, *J.Clin.Invest.* 71: 1836–1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IX a or Xa. Alternatively, as described by Bjoern et al. (Research Disclosure, 269 September 1986, pp. 564–565), factor VII may be activated by passing it through an ion-exchange chromatography column, such as Mono Q® (Pharmacia fine Chemicals) or the like. Modified or Inactivated FVIIa (FVIIai) May be Produced by the Following Methods:

International Application No. WO 92/15686 relates to modified Factor VIIa, polynucleic acid and mammalian cell lines for the production of modified Factor VIIa, and compositions comprising modified Factor VIIa for inhibiting blood coagulation.

Modified Factor VII may be encoded by a polynucleotide molecule comprising two operatively linked sequence coding regions encoding, respectively, a pre-pro peptide and a gla domain of a vitamin K-dependent plasma protein, and a gla domain-less Factor VII protein, wherein upon expression said polynucleotide encodes a modified Factor VII molecule which does not significantly activate plasma Factors X or IX, and is capable of binding tissue factor.

The catalytic activity of Factor VIIa can be inhibited by chemical derivatization of the catalytic centre, or triad. Derivatization may be accomplished by reacting Factor VII with an irreversible inhibitor such as an organophosphor compound, a sulfonyl fluoride, a peptide halomethyl ketone or an azapeptide, or by acylation, for example. Preferred peptide halomethyl ketones include PPACK (D-Phe-Pro-Arg chloromethyl-ketone; (see U.S. Pat. No. 4,318,904, incorporated herein by reference), D-Phe-Phe-Arg and Phe-Phe-Arg chloromethylketone (FFR-cmk); and DEGRck (dansyl-Glu-Gly-Arg chloromethylketone).

The catalytic activity of Factor VIIa can also be inhibited by substituting, inserting or deleting amino acids. In preferred embodiments amino acid substitutions are made in the amino acid sequence of the Factor VII catalytic triad, defined herein as the regions, which contain the amino acids, which contribute to the Factor VIIa catalytic site. The substitutions, insertions or deletions in the catalytic triad are generally at or adjacent to the amino acids which form the catalytic site. In the human and bovine Factor VII proteins, the amino acids, which form a catalytic "triad", are $Ser_{344}$, $Asp_{242}$, and $His_{193}$ (subscript numbering indicating position in the sequence). The catalytic sites in Factor VII from other mammalian species may be determined using presently available techniques including, among others, protein isolation and amino acid sequence analysis. Catalytic sites may also be determined by aligning a sequence with the sequence of other serine proteases, particularly chymotrypsin, whose active site has been previously determined (Sigler et al., *J. Mol. Biol.*, 35:143–164 (1968), incorporated herein by reference), and there from determining from said alignment the analogous active site residues. p In preferred embodiments of human and bovine Factor VII, the active site residue $Ser_{344}$ is modified, replaced with Gly, Met, Thr, or more preferably, Ala. Such substitution could be made separately or in combination with substitution(s) at other sites in the catalytic triad, which includes $His_{193}$ and $Asp_{242}$.

The amino acids, which form the catalytic site in Factor VII, such as $Ser_{344}$, $Asp_{242}$, and $His_{193}$ in human and bovine Factor VII, may either be substituted or deleted. Within the present invention, it is preferred to change only a single amino acid, thus minimizing the likelihood of increasing the antigenicity of the molecule or inhibiting its ability to bind tissue factor, however two or more amino acid changes (substitutions, additions or deletions) may be made and combinations of substitution(s), addition(s) and deletion(s) may also be made. In a preferred embodiment for human and bovine Factor VII, $Ser_{344}$ is preferably substituted with Ala, but Gly, Met, Thr or other amino acids can be substituted. It is preferred to replace Asp with Glu and to replace His with Lys or Arg. In general, substitutions are chosen to disrupt the tertiary protein structure as little as possible. The model of Dayhoff et al. (in *Atlas of Protein Structure* 1978, Nat'l Biomed. Res. Found., Washington, D.C.), incorporated herein by reference, may be used as a guide in selecting other amino acid substitutions. One may introduce residue alterations as described above in the catalytic site of appropriate Factor VII sequence of human, bovine or other species and test the resulting protein for a desired level of inhibition of catalytic activity and resulting anticoagulant activity as described herein. For the modified Factor VII the catalytic activity will be substantially inhibited, generally less than about 5% of the catalytic activity of wild-type Factor VII of the corresponding species, more preferably less than about 1%.

The modified Factor VII may be produced through the use of recombinant DNA techniques.

The amino acid sequence alterations may be accomplished by a variety of techniques. Modification of the DNA sequence may be by site-specific mutagenesis. Techniques for site-specific mutagenesis are well known in the art and are described by, for example, Zoller and Smith (*DNA* 3:479–488, 1984). Thus, using the nucleotide and amino acid sequences of Factor VII, one may introduce the alteration(s) of choice. The modified FVIIa may also be produced by chemical methods.

FFR-FVIIa (that is, D-Phe-Phe-Arg-FVIIa)

Example FFR Chloromethyl Ketone

Blockage of the active site of FVIIa with FFR chloromethyl ketone.

Blockage of the active site serine and histidine with chloromethyl ketone is a well-known method for irreversible inactivation of serine proteases. In order to optimise the blockage of a given protease it is important to choose a chloromethyl ketone derivative, which reacts specifically with the active site and with a fast on-rate. Such derivatives can be developed by attachment to the chloromethyl ketone group of an oligopeptide, which interacts, with the substrate-binding pocket of the particular serine protease of interest.

Glutamyl-Glycyl-Arginine chloromethyl ketone (EGR-ck or its Dansyl derivative, DEGR-ck) (S. Higashi, H. Nishimura, S. Fujii, K. Takada, S. Iwanaga, (1992) J. Biol. Chem. 267, 17990) or Prolyl-Phenyl-Arginine chloromethyl ketone (PFR-ck) (J. H. Lawson, S. Butenas, K. Mann, (1992) J. Biol. Chem. 267, 4834; J. Contrino, G. A. Hair, M. A. Schmeizl, F. R. Rickles, D. L. Kreutzer (1994) Am. J. Pathol. 145, 1315) have been applied as active site inhibitors of FVIIa. Compared with these chloromethyl ketones application of FFRck represents a rate increase of 10–70 fold.

The specificity of the reaction with FFR-chloromethyl ketone derivative of FVIIa was checked by HPLC and peptide mapping which showed that FVIIa had reacted with FFR-chloromethyl ketone in a 1:1 ratio such that >98% could be recovered as the expected product derivatized at histidine 193.

Inactivation of FVIIa by Various Chloromethyl Ketones:

3 μM FVIIa was incubated with 12 μM of chloromethyl ketone derivative in 50 mM TrisHCl, 100 mM NaCl, 5 mM $CaCl_2$, 0.01% Tween-80, pH 7.4. Samples were withdrawn at various time intervals as indicated and and diluted 20 times for activity measurements in 50 mM TrisHCl, 100 mM NaCl, 5 mM $CaCl_2$, 0.01% Tween-80, pH 7.4 containing 1 mM Ile-Pro-Arg-pNA. The residual FVIIa activity was measured by the increase in absorbance at 405 nm.

Usually, the mixture comprising the peptide or GLP-1 peptide and related impurities to be purified by ion exchange chromatography according to the present invention, will also contain amino acids, small peptides, large peptides, unrelated proteins, reactants, cell debris, HCP, endotoxins, and/or vira depending on whether recombinant DNA techniques and/or chemical modification techniques have been used or whether organic peptide synthetic chemistry techniques have been used.

Thus, any method, such as an industrial method, for producing a pure peptide or GLP-1 peptide, which includes an IEC process according to the present invention is also an aspect of the present application.

Accordingly, the present invention relates in a further aspect to an industrial method for producing a pure peptide or GLP-1 peptide, the method including a cation exchange chromatography process for purifying a peptide from a mixture comprising said peptide or GLP-1 peptide and related impurities, comprising the steps of:

separating said peptide or GLP-1 peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide or GLP-1 peptide has a positive local or overall net charge different from the local or overall positive net charge of said related impurities so as to remove said related impurities.

The present invention relates in a further aspect to a method for isolating a GLP-1 peptide, the method including purification of a GLP-1 peptide from a mixture comprising said peptide and related impurities via a cation exchange chromatography process, the cation exchange chromatography process comprising the step of:

separating said GLP-1 peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities; and subsequently, if necessary, subjecting to analytical tests and/or further purification, and isolating said peptide in a conventional manner.

The present invention relates in a further aspect to a method for isolating a GLP-1 peptide, the method including purification of a GLP-1 peptide from a mixture comprising said peptide and related or unrelated impurities via a cation exchange chromatography process, the cation exchange chromatography process comprising the step of:

separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities; and subsequently, if necessary, subjecting to analytical tests and/or further purification, and isolating said peptide in a conventional manner.

The present invention relates in a further aspect to an industrial method for producing a pure peptide or GLP-1 peptide, the method including an anion exchange chromatography process for purifying a peptide from a mixture comprising said peptide or GLP-1 peptide and related impurities, comprising the steps of:

separating said peptide or GLP-1 peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide or GLP-1 peptide has a negative local or overall net charge different from the local or overall negative net charge of said related impurities so as to remove said related impurities.

The present invention relates in a still further aspect to a method for isolating a GLP-1 peptide, the method including purification of a GLP-1 peptide from a mixture comprising said peptide and related impurities via an anion exchange chromatography process, the anion exchange chromatography process comprising the step of:

separating said GLP-1 peptide and said related impurities of said mixture by elution in a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities; and subsequently, if necessary, subjecting to analytical tests and/or further purification, and isolating said peptide in a conventional manner.

The present invention relates in a still further aspect to a method for isolating a GLP-1 peptide, the method including purification of a GLP-1 peptide from a mixture comprising said peptide and related or unrelated impurities via an anion exchange chromatography process, the anion exchange chromatography process comprising the step of:

separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities; and subsequently, if necessary, subjecting to analytical tests and/or further purification, and isolating said peptide in a conventional manner.

Any possible combination of two or more of the embodiments described herein, is comprised within the scope of the present invention.

The term "an organic modifier", as used herein, is intended to include an organic solvent or organic compound soluble in water or mixtures thereof, which modifier induces a favorable and changed selectivity between the unwanted related impurity or impurities and the GLP-1 peptide and the ion exchanger. Whether or not a selected modifier induces said selectivity will usually depend on the related impurity or impurities, and may be tested by trial-and-error. The organic modifier includes but is not limited to $C_{1-6}$-alkanol, $C_{1-6}$-alkenol or $C_{1-6}$-alkynol, urea, guanidine HCl, or $C_{1-6}$-alkanoic acid, such as acetic acid, $C_{2-6}$-glycol, $C_{3-7}$-polyalcohol including sugars, or mixtures thereof.

The term "$C_{1-6}$-alkanol", "$C_{1-6}$-alkenol" or "$C_{1-6}$-alkynol", as used herein, alone or in combination is intended to include those $C_{1-6}$-alkane, $C_{1-6}$-alkene or $C_{1-6}$-alkyne groups of the designated length in either a linear or branched or cyclic configuration whereto is linked a hydroxyl (-OH) (cf. Morrison & Boyd, Organic Chemistry, $4^{th}$ ed). Examples of linear alcohols are methanol, ethanol, n-propanol, allyl alcohol, n-butanol, n-pentanol and n-hexanol. Examples of branched alcohols are 2-propanol and tert-butyl alcohol. Examples of cyclic alcohols are cyclo propyl alcohol and 2-cyclohexen-1-ol.

The term "$C_{1-6}$-alkanoic acid", as used herein, is intended to include a group of the formula R' COOH wherein R' is H or $C_{1-5}$alkyl, such as acetic, propionic, butyric, methylbutyric, or valeric acid (cf. Morrison & Boyd, Organic Chemistry, $4^{th}$ ed).

The term "$C_{1-5}$-alkyl", as used herein, is intended to include a branched or straight alkyl group having from one to five carbon atoms. Typical $C_{1-5}$-alkyl groups include, but are not limited to, methyl, ethyl, n-propyl, iso-propyl, butyl, iso-butyl, sec-butyl, tert-butyl, pentyl, isopentyl, and the like (cf. Morrison & Boyd, Organic Chemistry, $4^{th}$ ed).

The term "$C_{2-6}$-glycol", as used herein, is intended to include a $C_{2-6}$-alkane containing two hydroxyl groups on different carbon atoms which may be adjacent or not. A typical $C_{2-6}$-glycol include, but is not limited to 1,2-ethanediol, 1,2-propanediol, or 2-methyl-2,4-pentanediol (cf. Morrison & Boyd, Organic Chemistry, $4^{th}$ ed).

The term "$C_{2-6}$-alkane", as used herein, is intended to include a branched or straight alkane group having from two to six carbon atoms. Typical $C_{2-6}$-alkane groups include, but are not limited to ethane, propane, iso-propane, butane, iso-butane, pentane, hexane and the like (cf. Morrison & Boyd, Organic Chemistry, $4^{th}$ ed).

The term "$C_{3-7}$-polyalcohol including sugars", as used herein, is intended to include a group of the formula $HOCH_2(CHOH)_nCH_2OH$ wherein n is an integer from 1–5, and monosaccharides such as mannose, glucose (cf. Morrison & Boyd, Organic Chemistry, $4^{th}$ ed).

The term "GLP-1 peptide", as used herein, is intended to designate GLP-1(7-37), GLP-1(7-36)amide as well as analogues and derivatives thereof, which are capable of being produced by conventional recombinant DNA techniques as well as conventional synthetic methods. Such GLP-1 peptides include but are not limited to native glucagon-like peptide-1, for instance such peptide fragments which comprises GLP-1(7-37) and functional derivatives thereof as disclosed in WO 87/06941; such peptide fragments which comprise GLP-1(7-36) and functional derivatives thereof as disclosed in WO 90/11296; such analogues of the active GLP-1 peptides 7-34, 7-35, 7-36, and 7-37 as disclosed in WO 91/11457; such GLP-1 derivatives in which a lipophilic substituent is attached to at least one amino acid residue as disclosed in WO 98/08871; such N-terminal truncated fragments of GLP-1 as disclosed in EP 0699686-A2; and such GLP-1 analogues and derivatives that include an N-terminal imidazole group as disclosed in EP 0708179-A2.

The term "GLP-2 peptide", as used herein, is intended to designate GLP-2(1-35), GLP-2(1-34), GLP-2(1-33) as well as analogues and derivatives thereof, which are capable of being produced by conventional recombinant DNA techniques as well as conventional synthetic methods. Such GLP-2 peptides include but are not limited to native glucagon-like peptide-2, GLP-2 derivatives in which a lipophilic substituent is attached to at least one amino acid residue as disclosed in WO 98/08872, human glucagon-like peptide-2 (hGLP-2), GLP-2(1-30); GLP-2(1-31); GLP-2(1-32); GLP-2(1-33); GLP-2(1-34), GLP-2(1-35), $Lys^{20}$GLP-2(1-35), $Lys^{20}Arg^{30}$GLP-2(1-33), $Arg^{30}Lys^{34}$GLP-2(1-34), $Arg^{30}Lys^{35}$GLP-2(1-35), $Arg^{30,35}Lys^{20}$GLP-2(1-35), $Arg^{35}$GLP-2(1-35), $Lys^{20}(N^{\epsilon}$-tetradecanoyl)GLP-2(1-33); $Lys^{20,30}$-bis$(N^{\epsilon}$-tetradecanoyl)GLP-2(1-33); $Lys^{20}(N^{\epsilon}$-tetradecanoyl)$Arg^{30}$GLP-2(1-33); $Arg^{30}Lys^{35}(N^{\epsilon}$-tetradecanoyl)GLP-2(1-35); $Arg^{30,35}Lys^{20}(N^{\epsilon}$-tetradecanoyl)GLP-2(1-35); $Arg^{35}Lys^{30}(N^{\epsilon}$-tetradecanoyl)GLP-2(1-35); $Arg^{30}Lys^{34}(N^{\epsilon}$-tetradecanoyl)GLP-2(1-34); $Lys^{20}((N^{\epsilon}$-($\omega$-carboxynonadecanoyl))GLP-2(1-33); $Lys^{20,30}$-bis$(N^{\epsilon}$-($\omega$-carboxynonadecanoyl))GLP-2(1-33); $Lys^{20}(N^{\epsilon}$-($\omega$-carboxynonadecanoyl))$Arg^{30}$GLP-2(1-33); $Arg^{30}Lys^{35}(N^{\epsilon}$-($\omega$-carboxynonadecanoyl))GLP-2(1-35); $Lys^{30}(N^{\epsilon}$-($\gamma$-glutamyl$(N^{\alpha}$-tetradecanoyl)))hGLP-2, $Lys^{30}(N^{\epsilon}$-($\gamma$-glutamyl$(N^{\alpha}$-hexadecanoyl)))hGLP-2, $Arg^{30,35}Lys^{20}(N^{\epsilon}$-($\omega$-carboxynonadecanoyl))GLP-2(1-35); $Arg^{35}Lys^{30}(N^{\epsilon}$-($\omega$-carboxynonadecanoyl))GLP-2(1-35); and $Arg^{30}Lys^{34}(N^{\epsilon}$-($\omega$-carboxynonadecanoyl))GLP-2(1-34).

The term "analogues" as used herein, is intended to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both.

The term "derivatives" as used herein, is intended to designate a peptide in which one or more of the amino acid residues of the parent peptide have been chemically modified, e.g. by alkylation, acylation, ester formation or amide formation or the like.

The term "salt component" as used herein, is intended to include any organic or inorganic salt, including but not limited to NaCl, KCl, $NH_4Cl$, $CaC_2$, sodium acetate, potassium acetate, ammonium acetate, sodium citrate, potassium citrate, ammonium citrate, sodium sulphate, potassium sulphate, ammonium sulphate, calcium acetate or mixtures thereof (cf. Remington's Pharmaceutical Sciences, Gennaro, ed., Mack Publishing Co., Easton, Pa., 1990, or Remington: The Science and Practice of Pharmacy, 19th Edition (1995), or handbooks from Amersham-Pharmacia Biotech).

The term "a buffer" as used herein, is intended to include any buffer including but not limited to: citrate buffers, phosphate buffers, tris buffers, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof (cf. Remington's Pharmaceutical Sciences, Gennaro, ed., Mack Publishing Co., Easton, Pa., 1990, or Remington:

The Science and Practice of Pharmacy, 19th Edition (1995), or handbooks from Amersham-Pharmacia Biotech).

The choice of starting pH, buffer and ionic strength is done according to well-known techniques such as conventional test-tube methods, cf. e.g. handbooks from Amersham-Pharmacia Biotech. The chromatographic ion exchange resin is chosen depending on the specific GLP-1 peptide to be purified and the conditions employed, such as pH, buffer, ionic strength etc., which are known to the person skilled in the art (that is, typically, pH below the isoelectric point (pI) of the GLP-1 peptide for cation exchange resins and pH above pI of the GLP-1 peptide for anion exchange resins, a sufficient buffer strength to maintain the desired pH, and a sufficiently low ionic strength possibly induced by the salt concentration), and includes but is not limited to Sepharose resins, Sephadex resins, Streamline resins, and Source resins from Amersham-Pharmacia Biotech, HyperD resins, Trisacryl resins, and Spherosil resins from BioSepra, TSKgel resins and Toyopearl resins from TosoHaas, Fractogel EMD resins from Merck, Poros resins from Perseptive Biosystems, Macro-Prep resins from BioRAD, Express-ion resins from Whatman etc.

The term "a solution consisting essentially of an organic modifier, water, optionally a salt component and optionally a buffer" as used herein, is intended to mean a solution containing one or more organic modifiers, water, one or more salt components or no salt component and one or more buffers or no buffer, and optionally one or more further conventional components which the person skilled in the art would consider adding, according to conventional ion exchange chromatography processes.

The term "related impurities" as used herein, is intended to mean one or more impurities with a different local or overall net charge from the GLP-1 peptide, for instance truncated forms, all kinds of extended forms (extra amino acids, various derivatives including esters etc.), deamidated forms, incorrectly folded forms, forms with undesired glycosylation including sialylation, and others. It follows then that "unrelated impurities" as used herein, is intended to cover impurities which are different from related impurities.

The term "a constant pH-value", as used herein is intended to mean that the pH-value may be constant, such as in the presence of a buffer or may vary typically within 3 pH units, if no buffer is present.

The term "with a linear or step pH-gradient", as used herein is intended to mean that the pH-value changes during the elution from a lower to a higher pH, or from a higher to a lower pH. Such change in pH is usually generated with a buffer and/or by addition of an inorganic or organic acid or base, e.g. HCl, NaOH, $H_2O$, acetic acid, $NH_3$, KOH, $H_2SO_4$, citric acid. A pH gradient for cation exchange would usually be from a lower to a higher pH, and for anion exchange from a higher to a lower pH.

The term "with a linear or step gradient or isocratically in salt component", as used herein is intended to mean that the salt concentration changes during the elution from a lower to a higher concentration or is constant.

The present invention also relates to the following aspects:

Aspect 1. A cation exchange chromatography process for purifying a GLP-1 peptide from a mixture comprising said peptide and related or unrelated impurities, comprising the step of:
separating said GLP-1 peptide and said related or unrelated impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related or unrelated impurities so as to remove said related or unrelated impurities.

Aspect 2. A cation exchange chromatography process for purifying a GLP-1 peptide from a mixture comprising said peptide and related impurities, comprising the step of:
separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities.

Aspect 3. An anion exchange chromatography process for purifying a GLP-1 peptide from a mixture comprising said peptide and related or unrelated impurities, comprising the step of:
separating said GLP-1 peptide and said related or unrelated impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related or unrelated impurities so as to remove said related or unrelated impurities.

Aspect 4. An anion exchange chromatography process for purifying a GLP-1 peptide from a mixture comprising said peptide and related impurities, comprising the step of:
separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities.

Aspect 5. The process according to any one of aspects 1–4 wherein the ratio of organic modifier to water on a weight percent basis is from 1:99 to 99:1.

Aspect 6. The process according to any one of aspects 1–5 wherein said organic modifier is selected from $C_{1-6}$-alkanol, $C_{1-6}$-alkenol or $C_{1-6}$-alkynol, urea, guanidine, or $C_{1-6}$-alkanoic acid, $C_{2-6}$-glycol, or $C_{3-7}$-polyalcohol including sugars.

Aspect 7. The process according to any one of aspects 1–6 wherein said salt component is selected from any organic or inorganic salt, preferably NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof.

Aspect 8. The process according to any one of aspects 1–6 wherein no salt component is present.

Aspect 9. The process according to any one of aspects 1–7 wherein said gradient in salt component is a step or linear gradient in the salt component.

Aspect 10. The process according to aspect 9 wherein said salt component is present in a concentration selected from the range of 0.1 mmol/kg to 3000 mmol/kg.

Aspect 11. The process according to any one of aspects –10 wherein said buffer is independently selected from citrate buffers, phosphate buffers, tris buffers, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof.

Aspect 12. The process according to any one of aspects 1–11 wherein said buffer is present in a concentration selected from the range of 0.1 mmol/kg to 500 mmol/kg.

Aspect 13. The process according to any one of aspects 1–10 wherein no buffer is present.

Aspect 14. A method for isolating a peptide, the method including purification of a GLP-1 peptide from a mixture comprising said peptide and related impurities via a cation exchange chromatography process, the cation exchange chromatography process comprising the steps of:
  separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities;
and subsequently, if necessary, subjecting to analytical tests and/or further purification, and isolating said peptide in a conventional manner.

Aspect 15. A method for isolating a peptide, the method including purification of a GLP-1 peptide from a mixture comprising said peptide and related impurities via an anion exchange chromatography process, the anion exchange chromatography process comprising the steps of:
  separating said GLP-1 peptide and said related impurities of said mixture by elution in a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a negative local or overall net charge different from the local or overall negative net charge of said related impurities so as to remove said related impurities;
and subsequently, if necessary, subjecting to analytical tests and/or further purification, and isolating said peptide in a conventional manner.

Aspect 16. The process or method according to any one of aspects 1–15 wherein said peptide to be purified is selected from GLP-1(7-37), GLP-1(7-36)amide as well as analogues and derivatives thereof.

EXAMPLES

The present invention is further illustrated by the following examples which, however, are not to be construed as limiting the scope of protection. The features disclosed in the foregoing description and in the following examples may, both separately and in any combination thereof, be material for realising the invention in diverse forms thereof.

Example 1

$Arg^{34}GLP-1_{(7-37)}$ was expressed in yeast (Sacch. cerevisiae) by conventional recombinant DNA technology e.g as described in WO 98/08871. $Arg^{34}GLP-1_{(7-37)}$ fermentation broth was purified by a conventional cation exchange chromatography capture step. The pool containing $Arg^{34}GLP-1_{(7-37)}$ and the truncated form, $Arg^{34}GLP-1_{(9-37)}$, as an impurity was adjusted to pH 3.1, and 1 ml of the resulting solution was applied to a 6.5 ml Ceramic S HyperD F (Bio-Sepra S. A.) column equilibrated with 32.5 ml 1.54% (w/w) tri-sodium citrate, 0.6% (w/w) succinic acid, 1.09% (w/w) di-sodium hydrogen phosphate di-hydrate, pH~3.2. The column was washed with 6.5 ml equilibration solution, and elution was performed with a linear pH gradient from 3.2 to 8.0 (1.54% (w/w) tri-sodium citrate, 0.6% (w/w) succinic acid, 1.09% (w/w) di-sodium hydrogen phosphate di-hydrate, pH 8.0) followed by 13 ml of isocratic elution at pH 8.0. A chromatogram is shown in FIG. 1. No distinct peaks or separation between the truncated form and the target GLP-1 moiety were obtained.

Example 2

$Arg^{34}GLP-1_{(7-37)}$ was expressed and captured by cation exchange as described in Example 1. The pool containing $Arg^{34}GLP-1_{(7-37)}$ and the truncated form, $Arg^{34}GLP-1_{(9-37)}$, as an impurity was adjusted to pH 3.1, and 1 ml of the resulting solution was applied to a 20 ml Source 30S (Amersham Pharmacia Biotech) column equilibrated with 100 ml 1.54% (w/w) tri-sodium citrate, 0.6% (w/w) succinic acid, 1.09% (w/w) di-sodium hydrogen phosphate di-hydrate, pH~3.2. The column was washed with 20 ml equilibration solution, and elution was performed with a linear pH gradient from 3.2 to 8.0 (1.54% (w/w) tri-sodium citrate, 0.6% (w/w) succinic acid, 1.09% (w/w) di-sodium hydrogen phosphate di-hydrate, pH 8.0) followed by 40 ml of isocratic elution at pH 8.0. No distinct peaks or separation between the truncated form and the target GLP-1 moiety were obtained.

Example 3

$Arg^{34}GLP-1_{(7-37)}$ was expressed and captured by cation exchange as described in Example 1. The pool containing $Arg^{34}GLP-1_{(7-37)}$ and the truncated form, $Arg^{34}GLP-1_{(9-37)}$, as an impurity was adjusted to pH 3.1, and 1 ml of the resulting solution was applied to a 20 ml Source 30S (Amersham Pharmacia Biotech) column equilibrated with 100 ml 0.77% (w/w) tri-sodium citrate, 0.3% (w/w) succinic acid, 0.55% (w/w) di-sodium hydrogen phosphate di-hydrate, pH~3.2. The column was washed with 20 ml equilibration solution. Elution was performed with a linear pH gradient from 3.2 to 8.0 (0.77% (w/w) tri-sodium citrate, 0.3% (w/w) succinic acid, 0.55% (w/w) di-sodium hydrogen phosphate di-hydrate) followed by 40 ml of isocratic elution at pH 8.0. Subsequent elution at pH 8.0 was performed with a linear salt gradient from 0.0 to 1.0 M NaCl (0.77% (w/w) tri-sodium citrate, 0.3% (w/w) succinic acid, 0.55% (w/w) di-sodium hydrogen phosphate di-hydrate, pH 8.0) followed by 40 ml of isocratic elution at 1.0 M NaCl. No distinct peaks or separation between the truncated form and the target GLP-1 moiety were obtained.

Example 4

Figure 2:
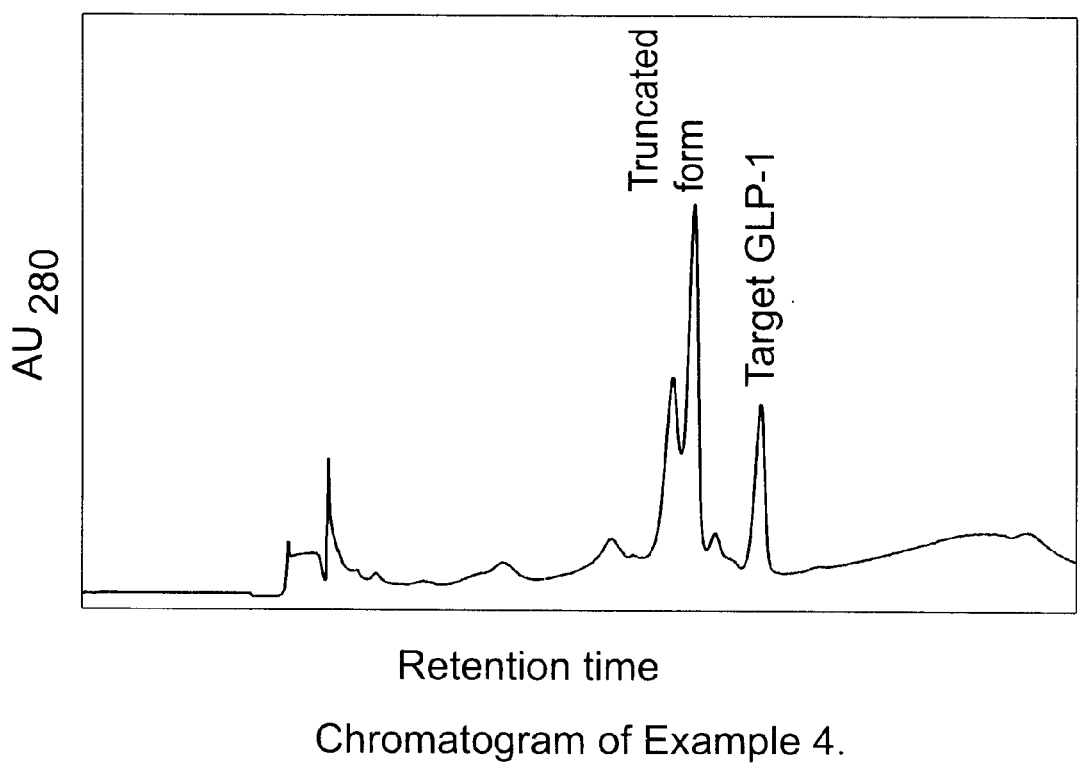

$Arg^{34}GLP-1_{(7-37)}$ was expressed and captured by cation exchange as described in Example 1. 2 volumes of water was added to the pool containing Arg$^{34}$GLP-1$_{(7-37)}$ and the truncated form, Arg$^{34}$GLP-1$_{(9-37)}$, as an impurity, and the solution was adjusted to pH 3.5. 25.5 ml of the resulting solution was applied to a 20 ml Source 30S (Amersham Pharmacia Biotech) column equilibrated with 100 ml 0.21% (w/w) tri-sodium citrate, 0.08% (w/w) succinic acid, 0.15% (w/w) di-sodium hydrogen phosphate di-hydrate, 45% (w/w) ethanol, pH~3.2. The column was washed with 20 ml equilibration solution, and elution was performed with a linear pH gradient from 3.2 to 8.0 (0.21% (w/w) tri-sodium citrate, 0.08% (w/w) succinic acid, 0.15% (w/w) di-sodium hydrogen phosphate di-hydrate, 45% (w/w) ethanol, pH 8.0) followed by 40 ml of isocratic elution at pH 8.0. A chromatogram is shown in FIG. 2. Distinct peaks and separation between the truncated form and the target GLP-1 moiety were obtained by addition of ethanol to the chromatographic solutions. Insignificant differences in set up between this and Example 2 are: different batch, pH, and aqueous dilution of the sample for application, higher load, and lower buffer concentration.

Example 5

Figure 3:
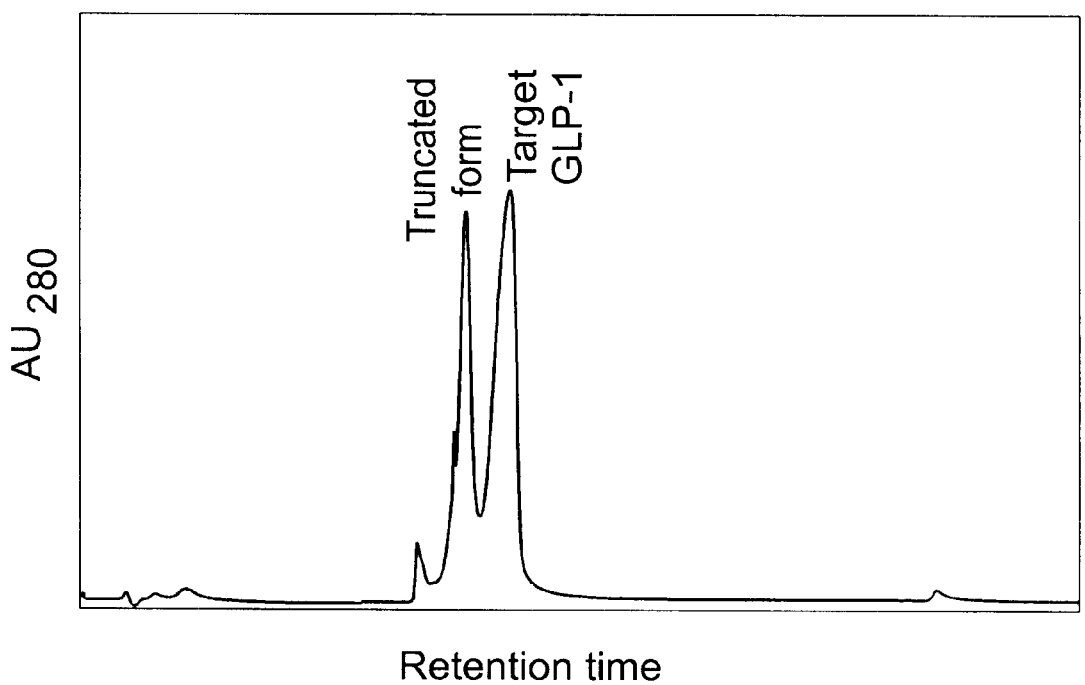

Arg$^{34}$GLP-1$_{(7-37)}$ was expressed and captured by cation exchange as described in Example 1. The pool containing Arg$^{34}$GLP-1$_{(7-37)}$ and the truncated form, Arg$^{34}$GLP-1$_{(9-37)}$, as an impurity was adjusted to pH 3.1, and 5 ml of the resulting solution was applied to a 20 ml Source 30S (Amersham Pharmacia Biotech) column equilibrated with 100 ml 0.85% (w/w) tri-sodium citrate, 0.33% (w/w) succinic acid, 0.6% (w/w) di-sodium hydrogen phosphate di-hydrate, 45% (w/w) ethanol, pH~3.2. The column was washed with 20 ml equilibration solution, and elution was performed with a linear pH gradient from 3.2 to 5.0 (0.85% (w/w) tri-sodium citrate, 0.33% (w/w) succinic acid, 0.6% (w/w) di-sodium hydrogen phosphate di-hydrate, 45% (w/w) ethanol) followed by 60 ml of isocratic elution at pH 8.0 (0.85% (w/w) tri-sodium citrate, 0.33% (w/w) succinic acid, 0.6% (w/w) di-sodium hydrogen phosphate di-hydrate, 45% (w/w) ethanol, pH 8.0). A chromatogram is shown in FIG. 3. Distinct peaks and separation between the truncated form and the target GLP-1 moiety were obtained by addition of ethanol to the chromatographic solutions.

RP-HPLC analysis for identification/verification of collected peaks was carried out on a C$_{18}$-substituted 120 Å silica (YMC) 4.0×250 mm column with 5 µm particles. Buffer A consisted of 0.15 M (NH$_4$)$_2$SO$_4$ in 7.8% (w/w) acetonitrile, pH 2.5, and buffer B contained 63.4% (w/w) acetonitrile. Linear gradients from 37–41% B in 12 min followed by 41–100% B in 15 min were run at a flow rate of 1 ml/min. The chromatographic temperature was kept at 60° C. and UV detection was performed at 214 nm. Analytical results were:

|  | Arg$^{34}$GLP-1$_{(7-37)}$ content | Arg$^{34}$GLP-1$_{(9-37)}$ content |
| --- | --- | --- |
| Sample for application | 36% | 13% |
| Impurity peak | 2% | 45% |
| Main peak | 50% | 1% |

Figure 4:
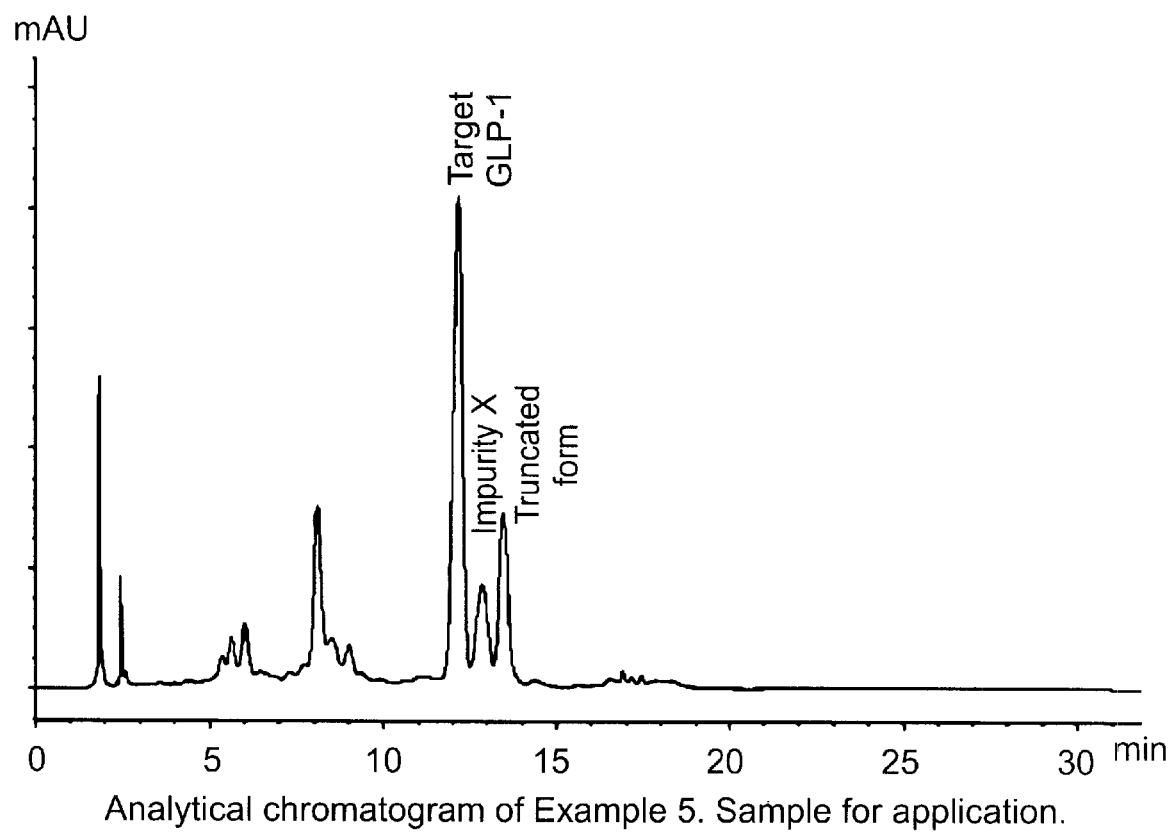
Figure 5:
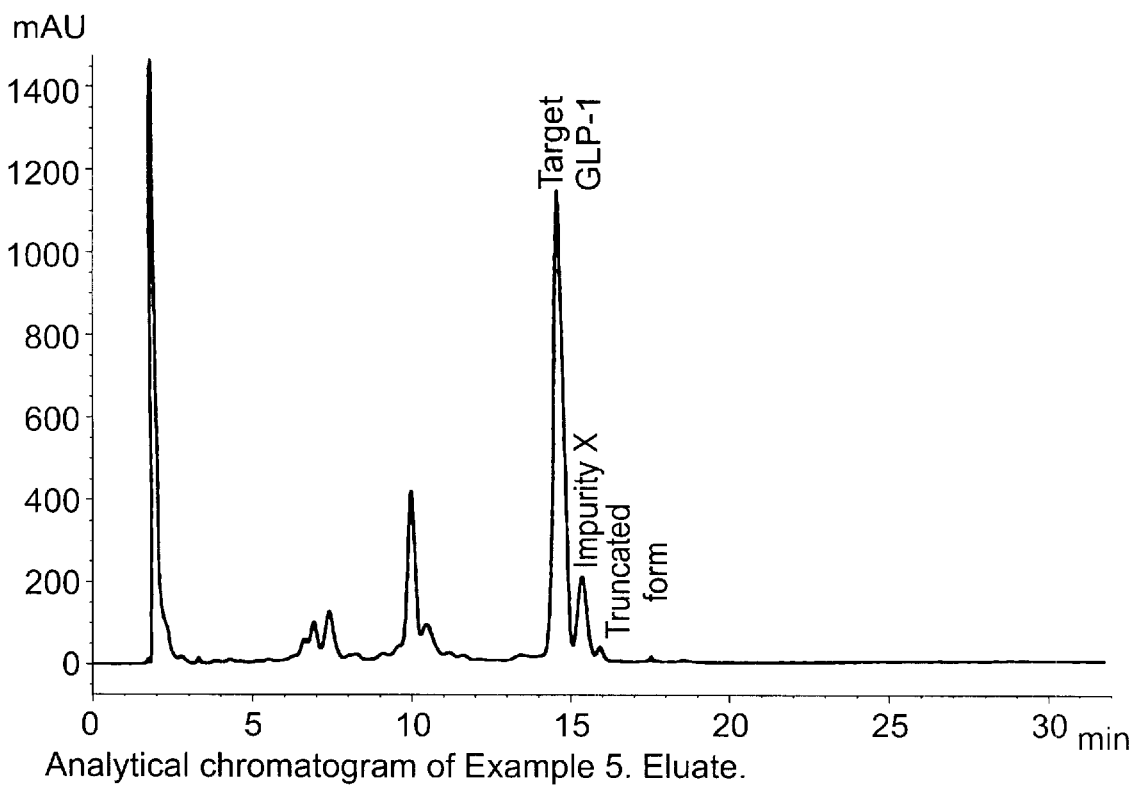

Chromatograms of the sample for application and the eluate is shown in FIGS. 4 and 5, respectively. The analytical results show a selective separation of the truncated form and a high reduction of the truncated form in the main peak containing the target GLP-1 moiety by cation exchange chromatography employing organic modifiers.

Example 6

Figure 6:
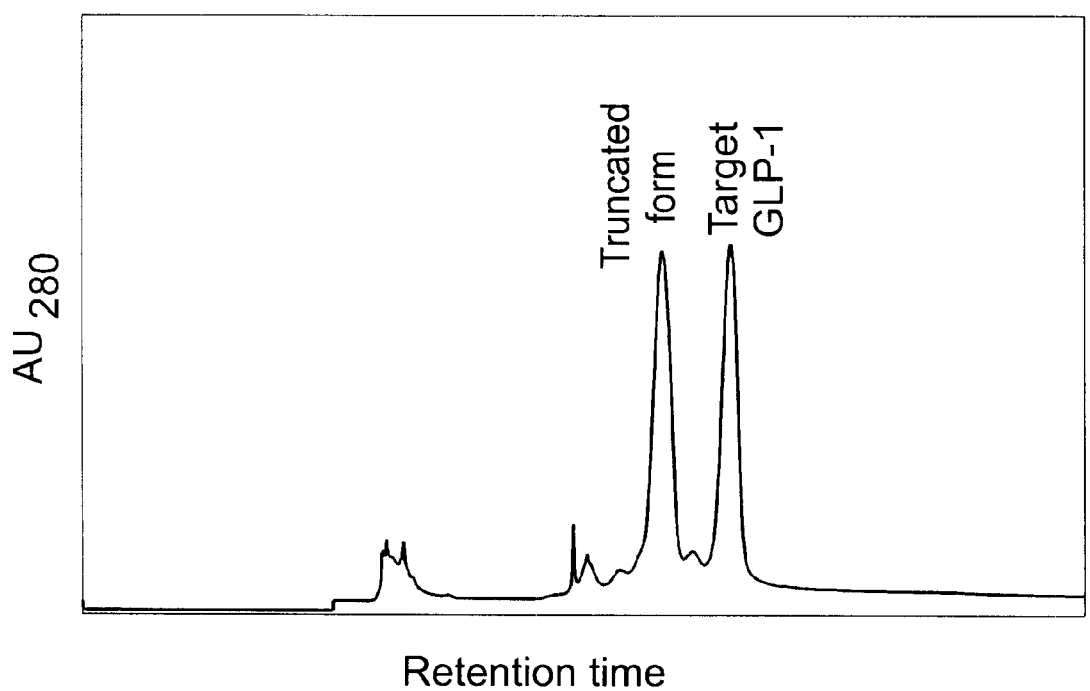

Arg$^{34}$GLP-1$_{(7-37)}$ was expressed and captured by cation exchange as described in Example 1. The pool containing Arg$^{34}$GLP-1$_{(7-37)}$ and the truncated form, Arg$^{34}$GLP-1$_{(9-37)}$, as an impurity was adjusted to pH 3.1, and 10 ml of the resulting solution was applied to a 20 ml Source 30S (Amersham Pharmacia Biotech) column equilibrated with 100 ml 20 mmol/kg citric acid, 45% (w/w) ethanol, pH 3.0. The column was washed with 20 ml equilibration solution, and elution was performed with a linear salt gradient from 0 to 250 mmol/kg KCl (20 mmol/kg citric acid, 45% (w/w) ethanol, pH 3.0) followed by 60 ml of isocratic elution at 250 mmol/kg KCl. A chromatogram is shown in FIG. 6. Distinct peaks and separation between the truncated form and the target GLP-1 moiety were obtained by addition of ethanol to the chromatographic solutions.

Example 7

Arg$^{34}$GLP-1$_{(7-37)}$ was expressed and captured by cation exchange as described in Example 1. The pool containing Arg$^{34}$GLP-1$_{(7-37)}$ and the truncated form, Arg$^{34}$GLP-1$_{(9-37)}$, as an impurity was adjusted to pH 3.5, and 10 ml of the resulting solution was applied to a 20 ml Source 30S (Amersham Pharmacia Biotech) column equilibrated with 100 ml 20 mmol/kg citric acid, 45% (w/w) ethanol, pH 3.5. The column was washed with 20 ml equilibration solution, and elution was performed with a linear salt gradient from 0 to 250 mmol/kg KCl (20 mmol/kg citric acid, 45% (w/w) ethanol, pH 3.5) followed by 40 ml of isocratic elution at 250 mmol/kg KCl. Distinct peaks and separation between the truncated form and the target GLP-1 moiety similar to Example 6 were obtained.

Example 8

Arg$^{34}$GLP-1$_{(7-37)}$ fermentation broth was purified by a conventional cation exchange chromatography capture step followed by a conventional RP-HPLC purification step. 6 volumes of water was added to the pool containing Arg$^{34}$GLP-1$_{(7-37)}$ and the truncated form, Arg$^{34}$GLP-1$_{(9-37)}$, as an impurity, and the solution was adjusted to pH 3.5. 170 ml of the resulting solution was applied to a 20 ml Source 30S (Amersham Pharmacia Biotech) column equilibrated with 100 ml 20 mmol/kg citric acid, 37.5 mmol/kg KCl, 45% (w/w) ethanol, pH 3.5. The column was washed with 20 ml equilibration solution, and elution was performed with a linear salt gradient from 37.5 to 162.5 mmol/kg KCl (20 mmol/kg citric acid, 45% (w/w) ethanol, pH 3.5) followed by 20 ml of isocratic elution at 250 mmol/kg KCl (20 mmol/kg citric acid, 45% (w/w) ethanol, pH 3.5). Distinct peaks and separation between the truncated form and the target GLP-1 moiety were obtained by addition of ethanol to the chromatographic solutions.

Example 9

Arg$^{34}$GLP-1$_{(7-37)}$ was expressed and captured by cation exchange as described in Example 1. 10 ml of the pool containing Arg$^{34}$GLP-1$_{(7-37)}$ and various impurities was applied to a 20 ml DEAE HyperD 20 (BioSepra S. A.) column equilibrated with 100 ml 20 mM di-sodium hydrogen phosphate di-hydrate, pH 7.5. The column was washed with 20 ml equilibration solution, and elution was performed with a linear salt gradient from 0 to 250 mM NaCl (20 mM di-sodium hydrogen phosphate di-hydrate, pH 7.5) followed by 40 ml of isocratic elution with 1 M NaCl (20 mM di-sodium hydrogen phosphate di-hydrate, pH 7.5). No distinct peaks or separation were obtained as the target GLP-1 moiety was eluting during all of the peak area.

Example 10

Figure 7:
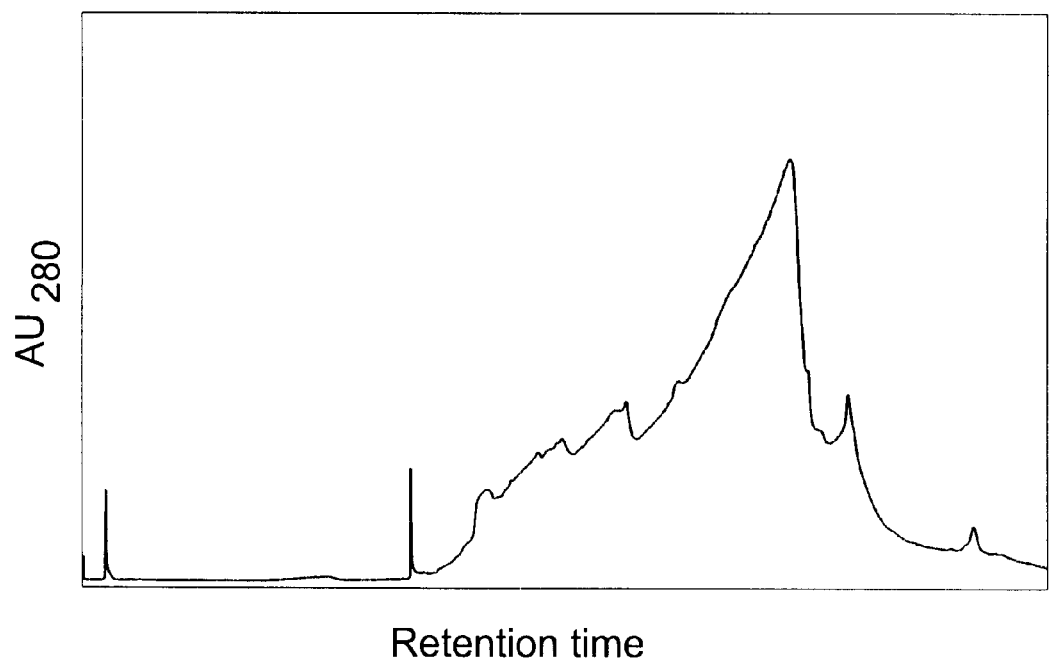

Arg$^{34}$GLP-1$_{(7-37)}$ was expressed and captured by cation exchange as described in Example 1. The pool containing Arg$^{34}$GLP-1$_{(7-37)}$ and various impurities was diluted with three volumes of water, and 40 ml of the resulting solution was applied to a 20 ml Source 15Q (Amersham Pharmacia Biotech) column equilibrated with 100 ml 20 mM Tris-hydroxymethyl amino-methane, pH 8.5. The column was washed with 20 ml equilibration solution, and elution was performed with a linear salt gradient from 0 to 250 mM NaCl (20 mM Tris-hydroxymethyl amino-methane, pH 8.5) followed by 40 ml of isocratic elution with 250 mM NaCl. A chromatogram is shown in FIG. 7. No distinct peaks or separation were obtained as the target GLP-1 moiety was eluting during all of the peak area.

Example 11

Figure 8:
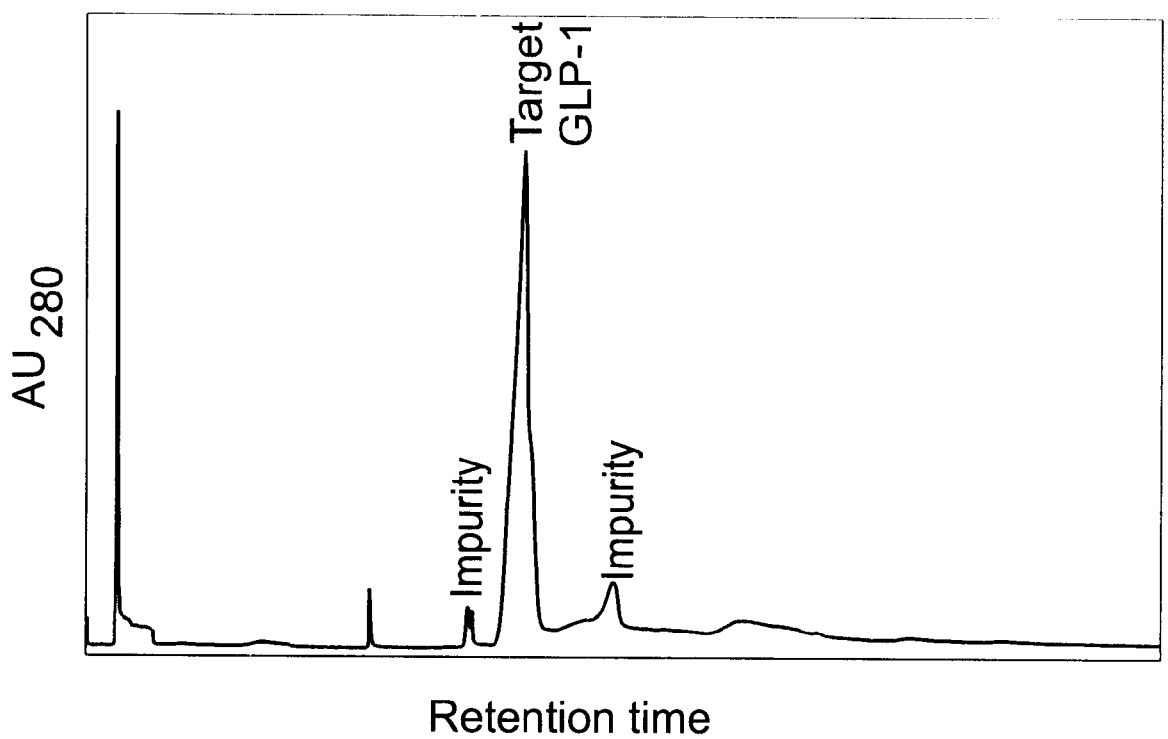

Arg$^{34}$GLP-1$_{(7-37)}$ was expressed and captured by cation exchange as described in Example 1. The pool containing Arg$^{34}$GLP-1$_{(7-37)}$ and various impurities was diluted with three volumes of water, and 20 ml of the resulting solution was applied to a 20 ml Source 15Q (Amersham Pharmacia Biotech) column equilibrated with 100 ml 20 mmol/kg Tris-hydroxymethyl amino-methane, 45% (w/w) ethanol, pH 8.5. The column was washed with 20 ml equilibration solution, and elution was performed with a linear salt gradient from 0 to 250 mmol/kg NaCl (20 mmol/kg Tris-hydroxymethyl amino-methane, 45% (w/w) ethanol, pH 8.5) followed by 40 ml of isocratic elution with 250 mmol/kg NaCl. A chromatogram is shown in FIG. 8. Distinct peaks and separation between various impurities and the target GLP-1 moiety were obtained by addition of ethanol to the chromatographic solutions. Insignificant differences in set up between this and Example 10 are: different load and buffer concentration.

Example 12

Arg$^{34}$GLP-1$_{(7-37)}$ was expressed and captured by cation exchange as described in Example 1. The pool containing Arg$^{34}$GLP-1$_{(7-37)}$ and various impurities was diluted with one volume of water and two volumes of ethanol, and 20 ml of the resulting solution was applied to a 20 ml Source 15Q (Amersham Pharmacia Biotech) column equilibrated with 100 ml 20 mmol/kg Tris-hydroxymethyl amino-methane, 45% (w/w) ethanol, pH 8.5. The column was washed with 20 ml equilibration solution, and elution was performed with a linear salt gradient from 0 to 100 mmol/kg NaCl (20 mmol/kg Tris-hydroxymethyl amino-methane, 45% (w/w) ethanol, pH 8.5) followed by 40 ml of isocratic elution with 100 mM NaCl. Distinct peaks and separation between various impurities and the target GLP-1 moiety were obtained by addition of ethanol to the chromatographic solutions.

Example 13

Arg$^{34}$GLP-1$_{(7-37)}$ was expressed as described in Example 1. Arg$^{34}$GLP-1$_{(7-37)}$ was isolated from the fermentation broth by a conventional reverse phase chromatography capture step, and subsequently precipitated at the pI (isoelectric point) of Arg$^{34}$GLP-1$_{(7-37)}$.

Figure 9:
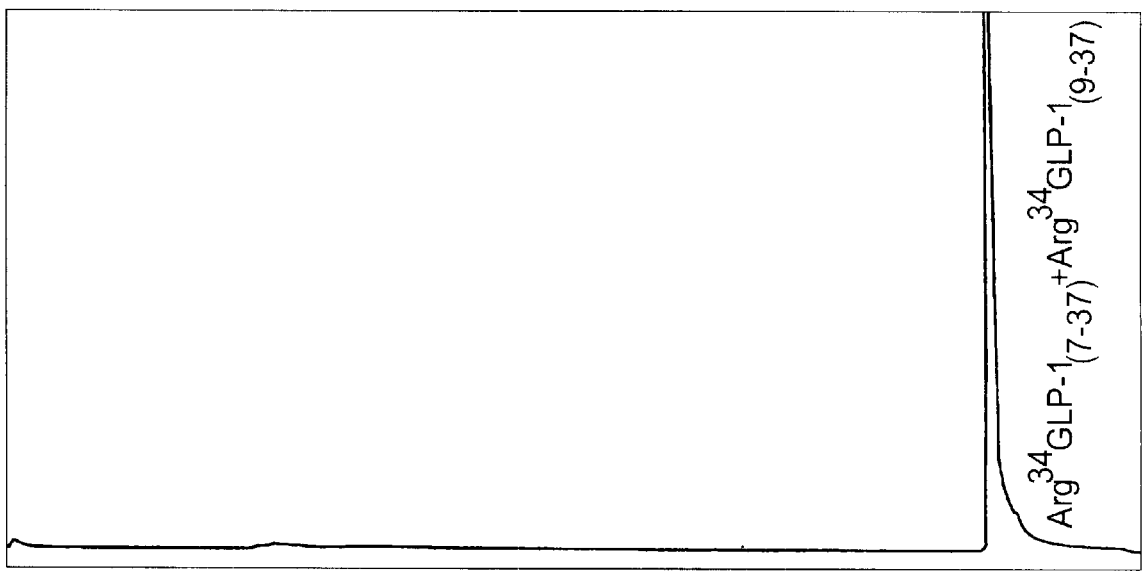

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, pH 3.5. The truncated form was not eluted/washed off by a linear gradient from 0 to 2 M NaCl (0.42% w/w citric acid, pH 3.5). The target peptide, Arg$^{34}$GLP-1$_{(7-37)}$, and the impurity, Arg$^{34}$GLP-1$_{(9-37)}$, were eluted in a single peak by 40 ml of the regeneration solvent 4% w/w NaOH. A chromatogram is shown in FIG. 9. No removal of the truncated impurity was achieved by the wash step at low pH with a conventional high salt solution without an organic modifier.

Example 14

Arg$^{34}$GLP-1$_{(7-37)}$ was isolated from the fermentation broth by conventional reverse phase chromatography and precipitated as described in Example 13.

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 34% w/w ethanol, pH 3.5. Elution was performed with a linear salt gradient from 0 to 2.23% w/w KCl (0.42% w/w citric acid, 34% w/w ethanol, pH 3.5). Distinct peaks and separation between the truncated form and the target GLP-1 moiety were obtained similar to Example 6.

Example 15

Arg$^{34}$GLP-1$_{(7-37)}$ was isolated from the fermentation broth by conventional reverse phase chromatography and precipitated as described in Example 13.

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 29% w/w ethanol, pH 3.5. Elution was performed with a linear salt gradient from 0 to 2.23% w/w KCl (0.42% w/w citric acid, 29% w/w ethanol, pH 3.5). Separation between the truncated form and the target GLP-1 moiety were obtained.

Example 16

Arg$^{34}$GLP-1$_{(7-37)}$ was isolated from the fermentation broth by conventional reverse phase chromatography and precipitated as described in Example 13.

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 51% w/w ethanol, pH 3.5. Elution was performed with a linear salt gradient from 0 to 2.23% w/w KCl (0.42% w/w citric acid, 51% w/w ethanol, pH 3.5). Distinct peaks and separation between the truncated form and the target GLP-1 moiety were obtained similar to Example 6.

Example 17

Arg$^{34}$GLP-1$_{(7-37)}$ was isolated from the fermentation broth by conventional reverse phase chromatography and precipitated as described in Example 13.

Figure 10:
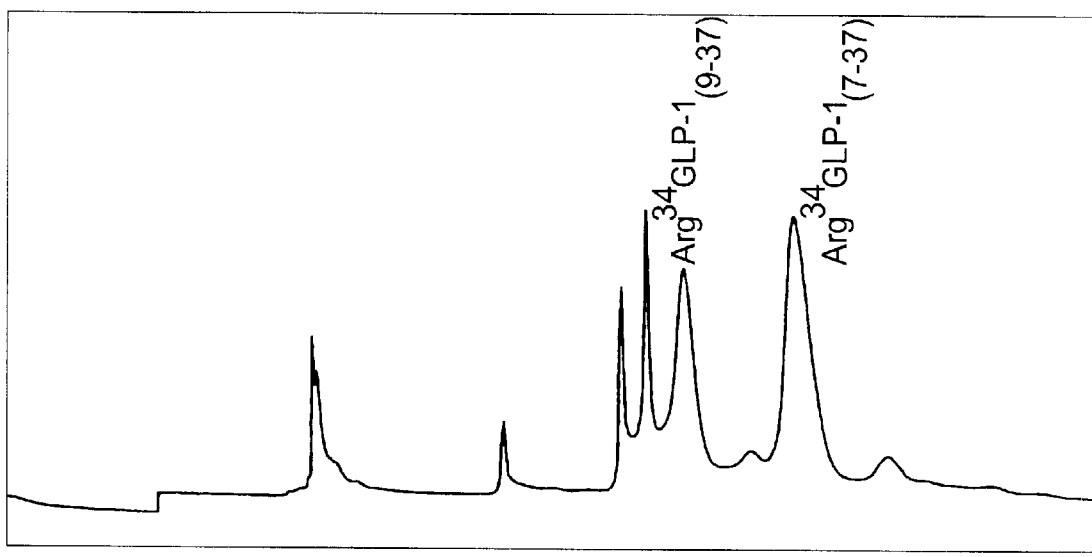

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 71% w/w ethanol, pH 3.5. Elution was performed with a linear salt gradient from 0 to 1.12% w/w KCl (0.42% w/w citric acid, 71% w/w ethanol, pH 3.5). A chromatogram is shown in FIG. 10. Distinct peaks and separation between the truncated form and the target GLP-1 moiety were obtained similar to Example 6.

Example 18

Arg$^{34}$GLP-1$_{(7-37)}$ was isolated from the fermentation broth by conventional reverse phase chromatography and precipitated as described in Example 13.

Figure 11:
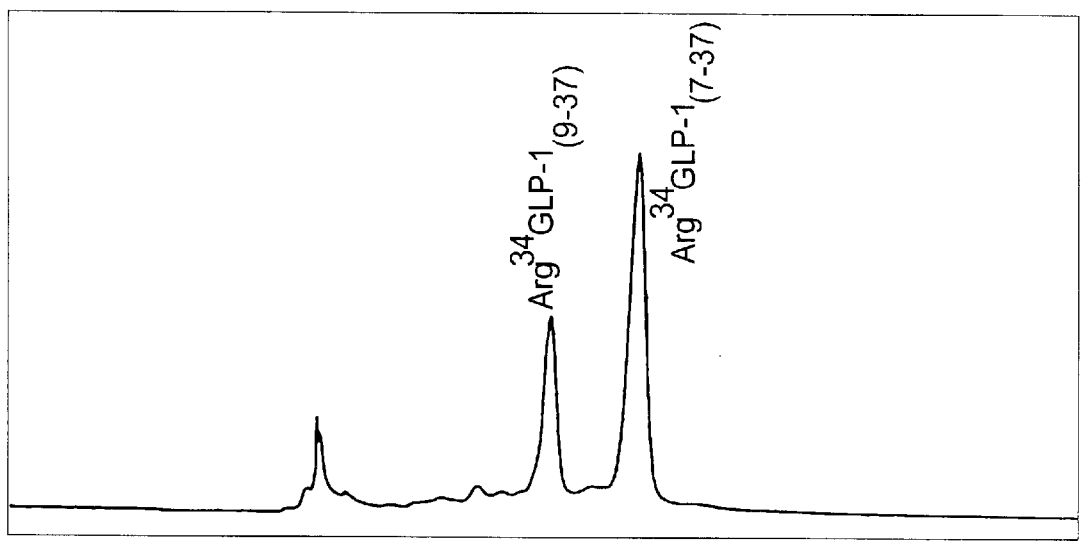

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 40% w/w 2-propanol, pH 3.5. Elution was performed with a linear salt gradient from 0 to 2.23% w/w KCl (0.42% w/w citric acid, 40% w/w 2-propanol, pH 3.5). A chromatogram is shown in FIG. 11. Distinct peaks and separation between the truncated form and the target GLP-1 moiety were obtained.

Example 19

Arg$^{34}$GLP-1$_{(7-37)}$ was isolated from the fermentation broth by conventional reverse phase chromatography and precipitated as described in Example 13.

Figure 12:
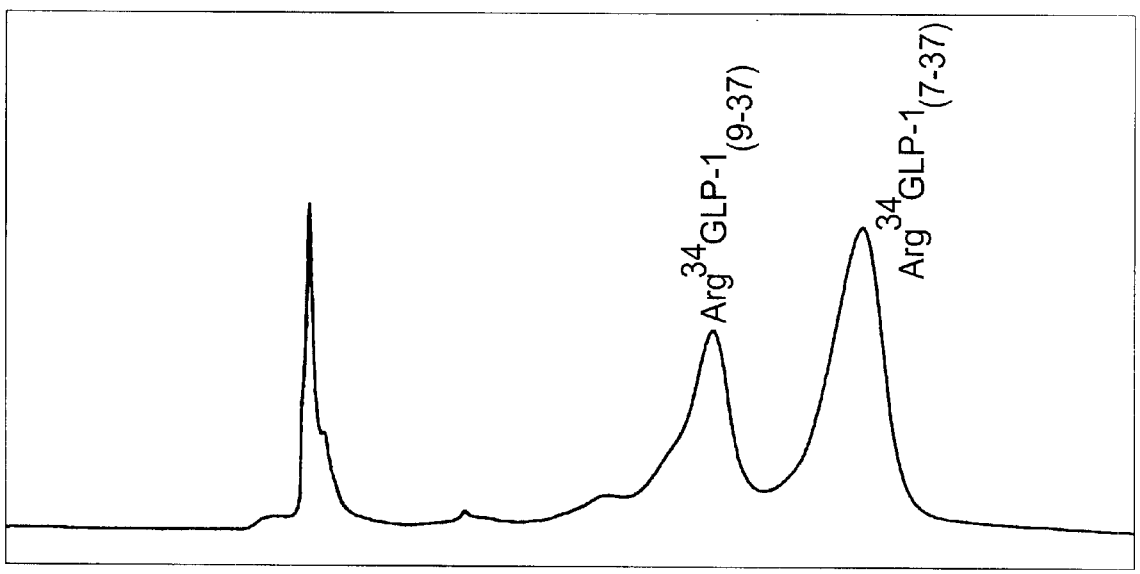

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 8 ml Poros 50 HS (PE Biosystems) column equilibrated with 24 ml 0.42% w/w citric acid, 51% w/w ethanol, pH 3.5. Elution was performed with a linear salt gradient from 0 to 2.23% w/w KCl (0.42% w/w citric acid, 51% w/w ethanol, pH 3.5). A chromatogram is shown in FIG. 12. Distinct peaks and separation between the truncated form and the target GLP-1 moiety were obtained.

Example 20

Arg$^{34}$GLP-1$_{(7-37)}$ was isolated from the fermentation broth by conventional reverse phase chromatography and precipitated as described in Example 13.

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 8 ml Poros 50 HS (PE Biosystems) column equilibrated with 24 ml 0.42% w/w citric acid, 40% w/w 2-propanol, pH 3.5. Elution was performed with a linear salt gradient from 0 to 2.23% w/w KCl (0.42% w/w citric acid, 40% w/w 2-propanol, pH 3.5). Distinct peaks and separation between the truncated form and the target GLP-1 moiety were obtained.

Example 21

Arg$^{34}$GLP-1$_{(7-37)}$ was isolated from the fermentation broth by conventional reverse phase chromatography and precipitated as described in Example 13.

Figure 13:
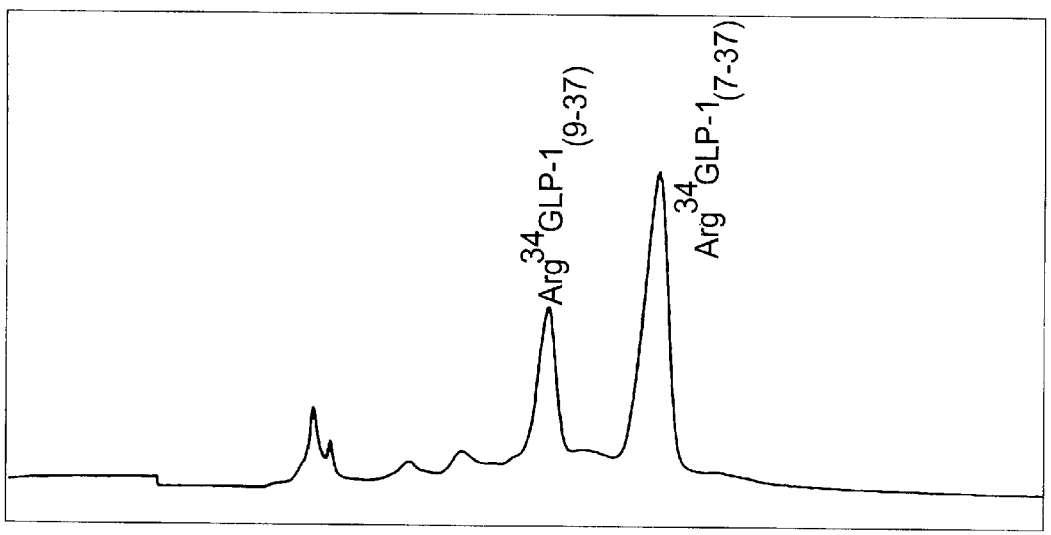

10 g of the precipitate containing Arg$^{34}$GLP-1$_{(7-37)}$ and the truncated form, Arg$^{34}$GLP-1$_{(9-37)}$, as one of several impurities was suspended in 500 ml water and dissolved by pH adjustment to 8.3 to a Arg$^{34}$GLP-1$_{(7-37)}$ concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 40% w/w 2-methyl-2,4-pentanediol, pH 3.5. Elution was performed with a linear salt gradient from 0 to 2.23% w/w KCl (0.42% w/w citric acid, 40% w/w 2-methyl-2,4-pentanediol, pH 3.5). A chromatogram is shown in FIG. 13. Distinct peaks and separation between the truncated form and the target GLP-1 moiety were obtained.

Example 22

Arg$^{34}$GLP-1$_{(7-37)}$ was isolated from the fermentation broth by conventional reverse phase chromatography and precipitated as described in Example 13. The precipitate was dissolved in water and purified by cation exchange chromatography using an organic modifier followed by a conventional reverse phase chromatography step in ethanol. Purified Arg$^{34}$GLP-1 (7-37) from the reverse phase eluate was precipitated at the pI of Arg$^{34}$GLP-1$_{(7-37)}$. Arg$^{34}$GLP-1$_{(7-37)}$ was acylated as described in WO 9808871.

Figure 14:
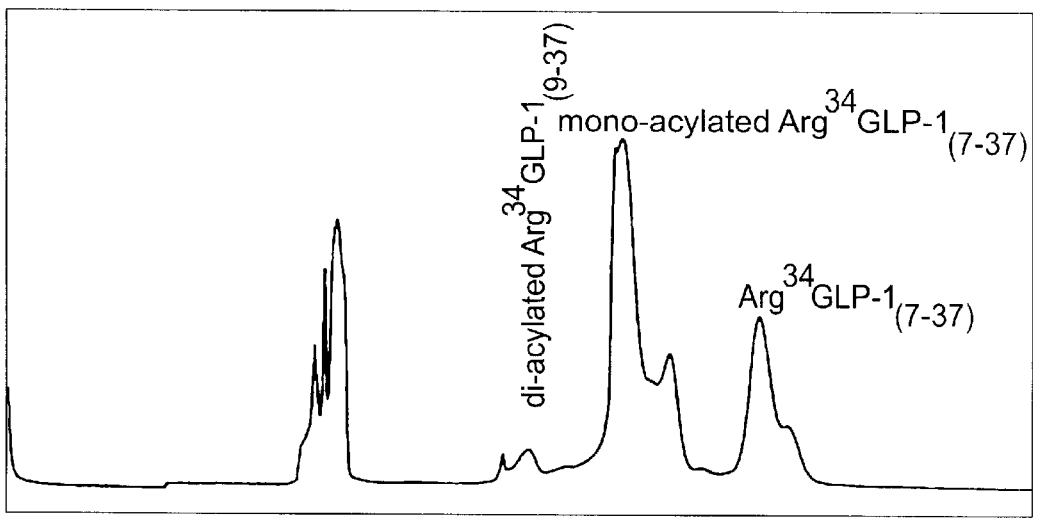

The resulting solution containing mono-acylated Arg$^{34}$GLP-1$_{(7-37)}$ in a concentration of 2 mg/ml, and Arg$^{34}$GLP-1$_{(7-37)}$ and di-acylated Arg$^{34}$GLP-1$_{(7-37)}$ as impurities, was diluted with 3 volumes of water. 5 ml of the diluted solution with pH 6.9 was applied to a 20 ml Source 30S (Amersham Pharmacia Biotech) column equilibrated with 60 ml 0.42% w/w citric acid, 64.5% w/w ethanol, pH 3.5. Elution was performed with a linear salt gradient from 0 to 1.30% w/w KCl (0.42% w/w citric acid, 64.5% w/w ethanol, pH 3.5). A chromatogram is shown in FIG. 14. The GLP-1 components eluted as distinct peaks and separation between the three GLP-1 moieties was obtained. RP-HPLC analysis for identification/verification of collected peaks was carried out on a dimethyl-butyl-dimethyl-silyl substituted 100 Å silica (Fuji-Davison) 4.0×250 mm column with 5 µm particles. Buffer A consisted of 0.15 M (NH$_4$)$_2$SO$_4$ in 7.8% (w/w) acetonitrile, pH 2.5, and buffer B contained 63.4% (w/w) acetonitrile. The gradient program at a flow rate of 1 ml/min was as follows: linear gradient from 35–57.5% B in 10 min, linear gradient from 57.5–67.5% B in 22 min, linear gradient from 67.5–90% B in 3 min, isocratic at 90% B in 5 min, linear gradient from 90–35% B in 2 min, and isocratic at 35% B in 5 min. The chromatographic temperature was kept at 60° C. and UV detection was performed at 214 nm. The analytical chromatograms verified the separation of the three GLP-1 moieties.

Example 23

Arg$^{34}$GLP-1$_{(7-37)}$ was isolated from the fermentation broth by conventional reverse phase chromatography and precipitated as described in Example 13. The precipitate was dissolved in water and purified by cation exchange chromatography using an organic modifier followed by a conventional reverse phase chromatography step in ethanol. Purified Arg$^{34}$GLP-1$_{(7-37)}$ from the reverse phase eluate was precipitated at the pI of Arg$^{34}$GLP-1$_{(7-37)}$. Arg$^{34}$GLP-1$_{(7-37)}$ was acylated as described in WO 9808871.

The resulting solution containing mono-acylated Arg$^{34}$GLP-1$_{(7-37)}$ in a concentration of 2 mg/ml, and Arg$^{34}$GLP-1$_{(7-37)}$ and di-acylated Arg$^{34}$GLP-1$_{(7-37)}$ as impurities, was diluted with 3 volumes of water. 5 ml of the diluted solution with pH 6.9 was applied to a 20 ml Source 30S (Amersham Pharmacia Biotech) column equilibrated with 60 ml 0.42% w/w citric acid, 40% w/w 2-propanol, pH 3.5. Elution was performed with a linear salt gradient from 0 to 2.23% w/w KCl (0.42% w/w citric acid, 40% w/w 2-propanol, pH 3.5). Separation between the three GLP-1 moieties was obtained.

The RP-HPLC analysis method of Example 22 was used for identification/verification of collected peaks.

What is claimed is:

1. A process for purifying a glucagon-like peptide 1 (GLP-1) from a mixture comprising said GLP-1 peptide and impurities, said method comprising:

eluting said GLP-1 peptide and said impurities of said mixture from a cation exchange chromatography matrix using a solution comprising an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said GLP-1 peptide has a positive local or overall net charge different from the local or overall positive net charge of said impurities so as to remove said impurities.

2. A method according to claim 1, further comprising subjecting said eluted peptide to analytical tests and/or further purification.

3. The process according to claim 1 wherein said GLP-1 peptide is selected from the group consisting of GLP-1(7-37), GLP-1(7-36)amide; and analogues and derivatives of either of the foregoing.

4. A process according to claim 3, wherein said GLP-1 analogue is selected from the group consisting of Arg$^{34}$GLP-1(7-37); Arg$^{26}$GLP-1(7-37); Arg$^{34}$Lys$^{26}$(N$^{\epsilon}$-(γ-Glu-(N$^{\alpha}$-tetradecanoyl)))GLP-1(7-37); Arg$^{34}$Lys$^{26}$(N$^{\epsilon}$-(γ-Glu-(N$^{\alpha}$-hexadecanoyl)))GLP-1(7-37); Arg$^{26}$Lys$^{34}$(N$^{\epsilon}$-(γ-Glu-(N$^{\alpha}$-tetradecanoyl)))GLP-1(7-37); Arg$^{26}$Lys$^{34}$(N$^{\epsilon}$-(γ-Glu-(N$^{\alpha}$-hexadecanoyl)))GLP-1(7-37); Val$^{8}$GLP-1(7-37); Thr$^{8}$GLP-1(7-37); Met$^{8}$GLP-1(7-37); Gly$^{8}$GLP-1(7-37); Val$^{8}$GLP-1(7-36)amide; Thr$^{8}$GLP-1(7-36)amide; Met$^{8}$GLP-1(7-36)amide; and Gly$^{8}$GLP-1(7-36)amide.

5. The process according to claim 1 wherein the ratio of organic modifier to water on a weight percent basis is from 1:99 to 99:1.

6. The process according to claim 1 wherein the ratio of organic modifier to water on a weight percent basis is from 20:80 to 80:20.

7. The process according to claim 1 wherein said organic modifier is selected from the group consisting of $C_{1-6}$-alkanol, $C_{1-6}$-alkenol or $C_{1-6}$-alkynol, urea, guanidine, or $C_{1-6}$-alkanoic acid, $C_{2-6}$-glycol, and $C_{3-7}$-polyalcohol including sugars.

8. A process for purifying a glucagon-like peptide 1 (GLP-1) from a mixture comprising said GLP-1 peptide and related impurities, said method comprising:

eluting said GLP-1 peptide and said related impurities of said mixture from a cation exchange chromatography matrix using a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said GLP-1 peptide has a positive local or overall net charge different from the local or overall positive net charge of said related impurities so as to remove said related impurities.

9. A process for purifying a peptide selected from the group consisting of FactorVII, FactorVIIa, FactorVIIai, and D-Phe-Phe-Arg-FactorVIIa from a mixture comprising said peptide and related impurities, said method comprising:

eluting said peptide and said related impurities of said mixture from a cation exchange chromatography matrix using a solution consisting essentially of an organic modifier, water, optionally a salt component, and optionally a buffer, with a linear or step gradient or isocratically in salt component and/or with a linear or step pH-gradient or at a constant pH-value, wherein the pH-gradient or pH-value should be in the range where said peptide has a positive local or overall net charge different from the local or overall positive net charge of said related impurities so as to remove said related impurities.

* * * * *